United States Patent
Herzog et al.

(10) Patent No.: US 11,419,804 B2
(45) Date of Patent: Aug. 23, 2022

(54) SUNSCREEN FORMULATIONS OPTIMIZED FOR THE FORMATION OF VITAMIN D

(71) Applicant: BASF SE, Ludwigshafen (DE)

(72) Inventors: Bernd Herzog, Grenzach-Wyhlen (DE); Dieter Kockott, Hanau (DE); Heike Flösser-Müller, Brasschaat (BE)

(73) Assignee: BASF SE, Ludwigshafen am Rhein (DE)

(*) Notice: Subject to any disclaimer, the term of this patent is extended or adjusted under 35 U.S.C. 154(b) by 86 days.

(21) Appl. No.: 15/327,071

(22) PCT Filed: Jul. 24, 2015

(86) PCT No.: PCT/EP2015/066985
§ 371 (c)(1),
(2) Date: Jan. 18, 2017

(87) PCT Pub. No.: WO2016/012586
PCT Pub. Date: Jan. 28, 2016

(65) Prior Publication Data
US 2018/0200170 A1    Jul. 19, 2018

(30) Foreign Application Priority Data

Jul. 25, 2014   (EP) .................................. 14178458

(51) Int. Cl.
*A61K 8/44* (2006.01)
*A61Q 17/04* (2006.01)
(Continued)

(52) U.S. Cl.
CPC ................ *A61K 8/445* (2013.01); *A61K 8/29* (2013.01); *A61K 8/35* (2013.01); *A61K 8/37* (2013.01);
(Continued)

(58) Field of Classification Search
None
See application file for complete search history.

(56) References Cited

U.S. PATENT DOCUMENTS

| 4,189,468 A | 2/1980 | Vanlerberghe et al. |
| 2011/0195036 A1 | 8/2011 | Clemente et al. |

(Continued)

FOREIGN PATENT DOCUMENTS

| DE | 1 165 574 B | 3/1964 |
| DE | 2 024 051 A1 | 12/1971 |

(Continued)

OTHER PUBLICATIONS

Herzog, B., et al., "In Silico Determination of Topical Sun Protection", Cosmetic Science Technology, 2011, pp. 62-71.
(Continued)

*Primary Examiner* — Dominic Lazaro
(74) *Attorney, Agent, or Firm* — Faegre Drinker Biddle & Reath LLP

(57) ABSTRACT

The present invention relates to a sunscreen formulation comprising at least one of the UV filters (A) selected from (a) triazine derivatives; (b) cinnamic acid derivatives; (c) bis-resorcinyl triazines; (f) benzimidazole derivatives; ($i_5$) 4-Methylbenzylidene Camphor; (h) benzoyl piperazine derivatives; (j) benzoxazole derivatives; (k) diarylbutadiene derivatives; (I) phenyl benzotriazole derivatives; (n) benzylidene malonates; ($o_3$) TEA-Salicylate; (r) imidazoline derivatives; (u) inorganic UV filters selected from metal oxides; (v) naphthalates; and (w) merocyanine derivatives; and optionally comprising at least one of the UV filters (B) selected from (d) aminobenzophenone derivatives; (e) dibenzoylmethane derivatives; (g) β,β-Diphenylacrylate derivatives; ($i_5$) camphor derivatives different from; ($o_3$) salicylate derivatives different from; (p) anthranilate derivatives; and (s) benzalmalonate derivatives; wherein the ratio
(Continued)

The ratio of the effective irradiance for vitamin $D_3$ formation and the effective irradiance for erythema formation R = $E_{pvD}/E_{er}$ under conditions of natural sunlight R of the effective irradiance for previtamin $D_3$ formation $E_{pvd}$ to the effective irradiance for erythema formation $E_{er}$ on the skin is at least 1.8, for increasing the transmittance of UV radiation on human skin for the production of cholecalciferol (previtamin $D_3$) and simultaneously for the use in a method for protecting the human skin against UV radiation when exposed to the sun, which method comprises applying said sunscreen formulation to the skin.

19 Claims, 5 Drawing Sheets

(51) Int. Cl.
- *A61K 8/49* (2006.01)
- *A61K 8/35* (2006.01)
- *A61K 8/29* (2006.01)
- *A61K 8/37* (2006.01)
- *A61K 8/41* (2006.01)
- *A61K 8/40* (2006.01)

(52) U.S. Cl.
CPC ............... *A61K 8/40* (2013.01); *A61K 8/415* (2013.01); *A61K 8/496* (2013.01); *A61K 8/4926* (2013.01); *A61K 8/4946* (2013.01); *A61K 8/4966* (2013.01); *A61Q 17/04* (2013.01)

(56) References Cited

U.S. PATENT DOCUMENTS

| | | | |
|---|---|---|---|
| 2011/0268678 A1* | 11/2011 | Armstrong | A61K 8/35 424/60 |
| 2011/0274632 A1 | 11/2011 | Ishitobi et al. | |
| 2012/0128611 A1* | 5/2012 | Grumelard | A61Q 17/04 424/60 |
| 2016/0067158 A1 | 3/2016 | Hloucha et al. | |

FOREIGN PATENT DOCUMENTS

| | | |
|---|---|---|
| EP | 2 407 163 A1 | 1/2012 |
| FR | 2 252 840 A1 | 6/1975 |
| GB | 962919 A | 7/1964 |
| GB | 1 333 475 A | 10/1973 |
| WO | WO-2010/076731 A2 | 7/2010 |
| WO | WO-2010/110020 A1 | 9/2010 |
| WO | WO-2010/125541 A1 | 11/2010 |
| WO | WO-2011/003774 A2 | 1/2011 |
| WO | WO-2011/097555 A1 | 8/2011 |
| WO | WO-2012/168275 A2 | 12/2012 |
| WO | WO-2014/070266 A1 | 5/2014 |

OTHER PUBLICATIONS

Stanfield, J., et al., "In Vitro Measurements of Sunscreen Protection", Photochemical & Photobiological Sciences, 2010, vol. 9, No. 4, pp. 489-494.

International Preliminary Report on Patentability for International Application No. PCT/EP2015/066985 dated Jan. 31, 2017.

International Search Report for PCT/EP2015/066985 dated Nov. 11, 2015.

Written Opinion of the International Searching Authority for PCT/EP2015/066985 dated Nov. 11, 2015.

* cited by examiner

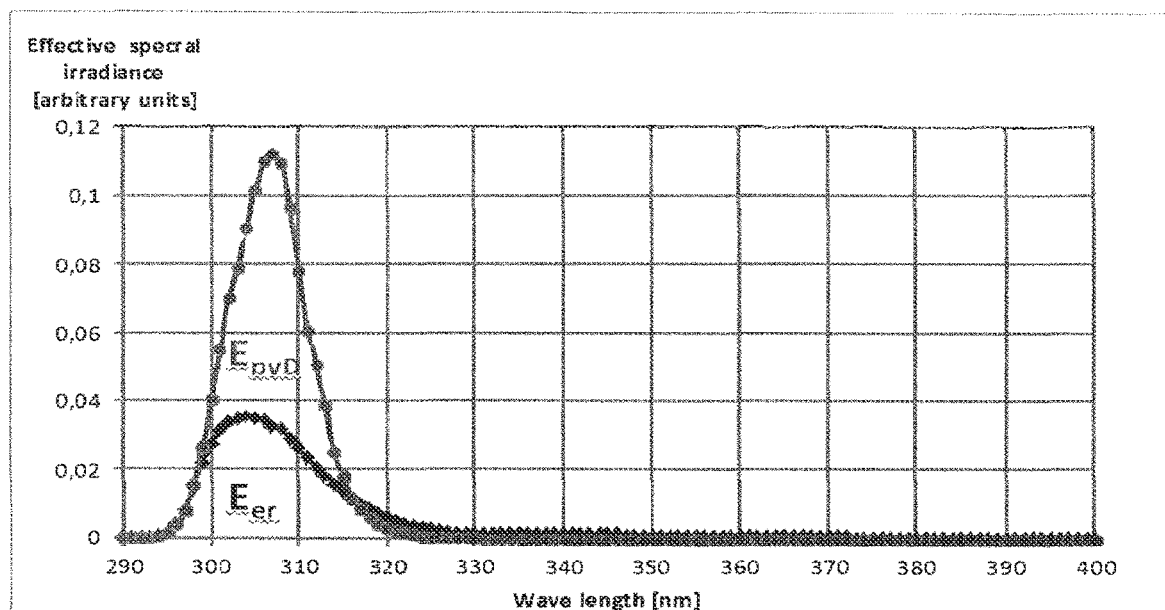
Fig. 1: The ratio of the effective irradiance for vitamin $D_3$ formation and the effective irradiance for erythema formation $R = E_{pvD}/E_{er}$ under conditions of natural sunlight

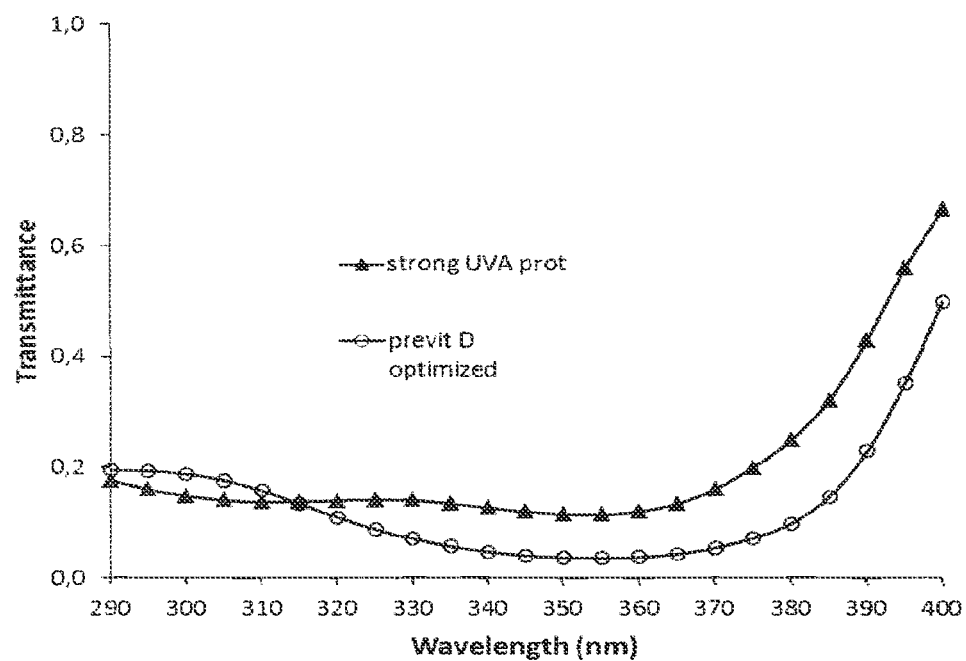
Fig. 2: Spectra of simulated UV transmittances of four SPF 6 sunscreens (compositions in Table 1) with strong UVA (A1.3) and vitamin $D_3$ optimized (A1.4) protective properties

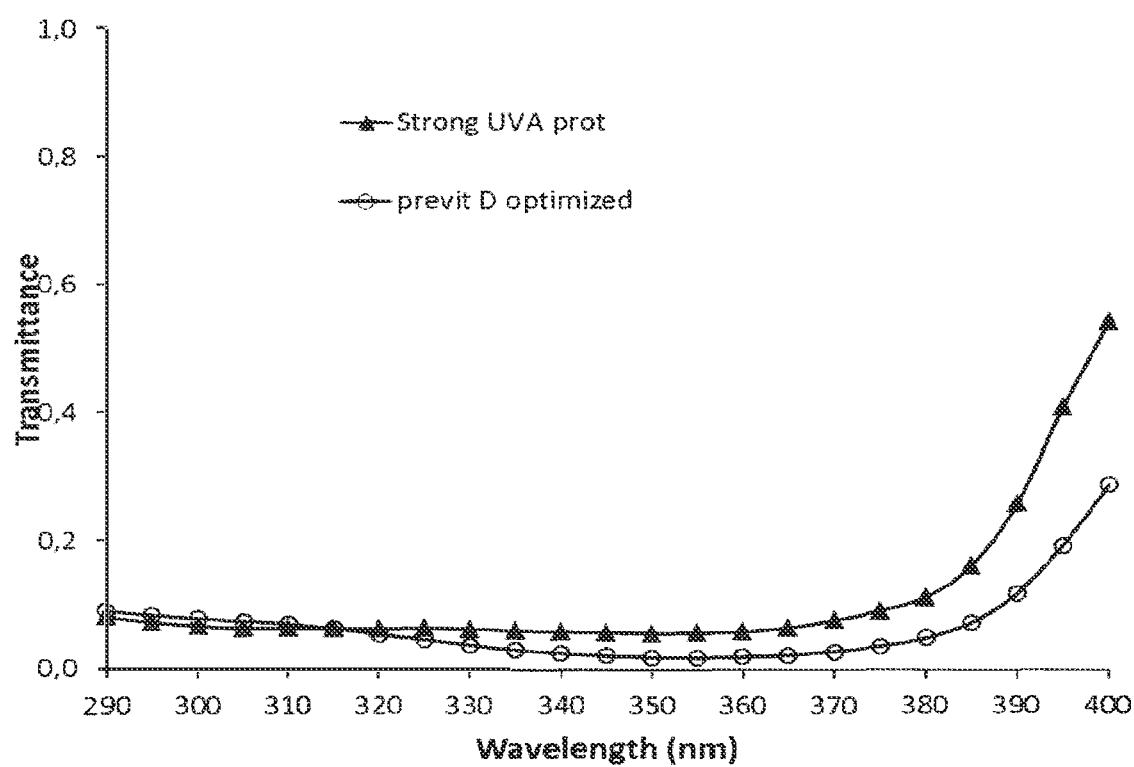
Fig. 3: Spectra of simulated UV transmittances of four SPF 15 sunscreens (compositions in Table 2) with strong UVA (A2.3) and vitamin $D_3$ optimized (A2.4) protective properties.

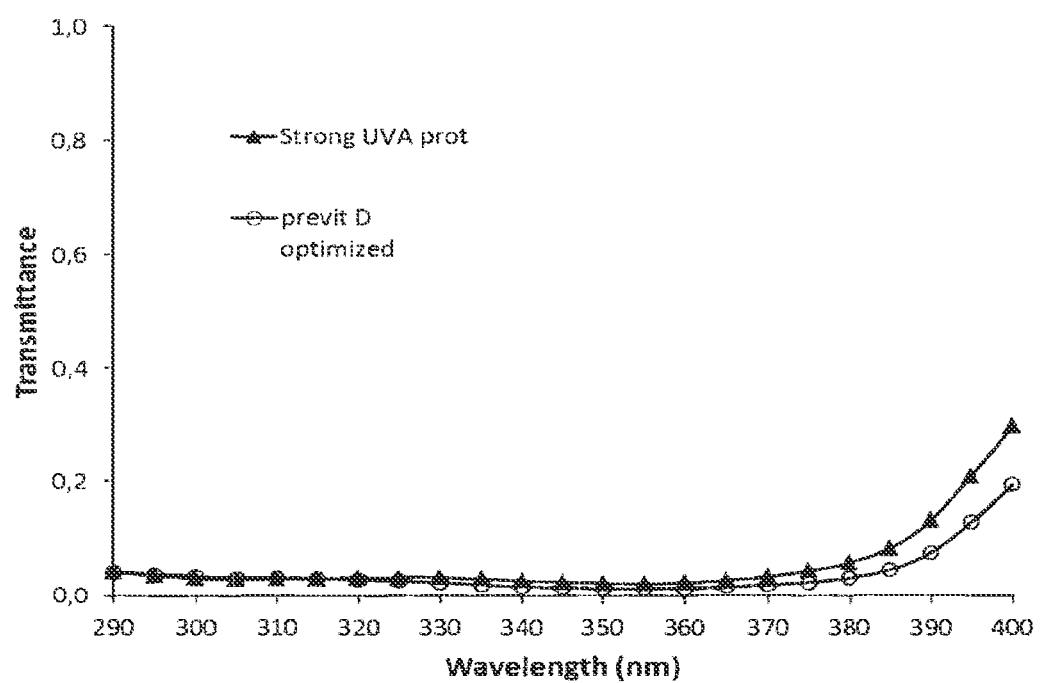
Fig. 4: Spectra of simulated UV transmittances of four SPF 30 sunscreens (compositions in Table 3) with strong UVA (A3.3) and Vitamin D optimized (A3.4) protective properties.

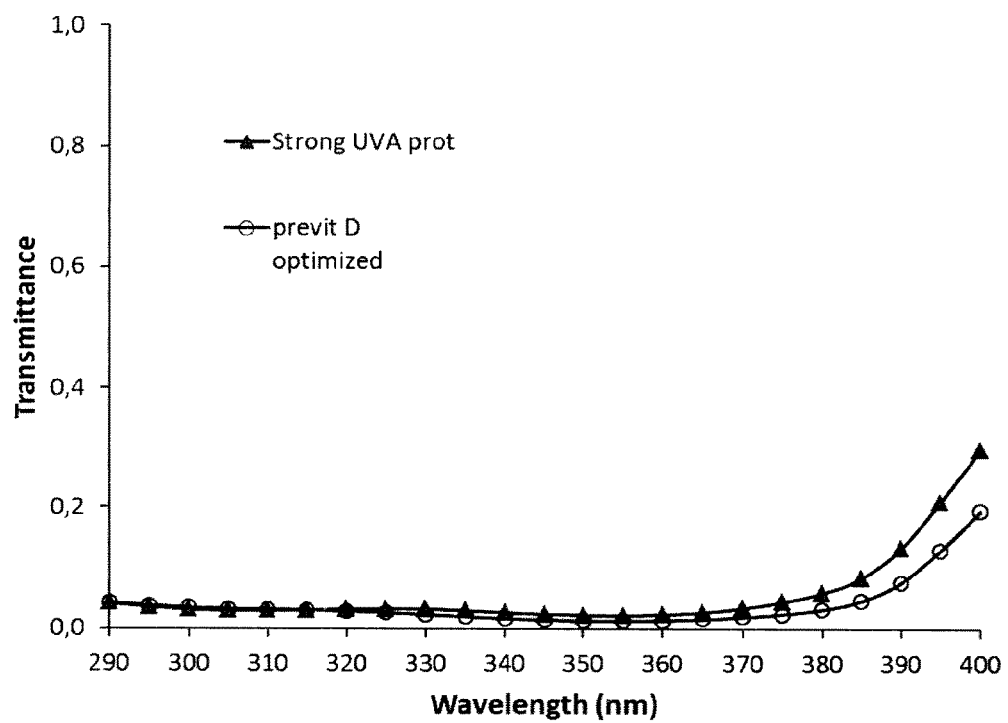
Figure 5: Spectra of simulated UV transmittances of four SPF 30 sunscreens (compositions in Table 3) with strong UVA (A3.3) and Vitamin D optimized (A3.4) protective properties.

SUNSCREEN FORMULATIONS OPTIMIZED
FOR THE FORMATION OF VITAMIN D

RELATED APPLICATIONS

This application is a national stage application (under 35 U.S.C. § 371) of PCT/EP2015/066985, filed Jul. 24, 2015, which claims benefit of European Application No. 14178458.7, filed Jul. 25, 2014.

BRIEF DESCRIPTION OF THE DRAWINGS

FIG. 1 shows the ratio of the effective irradiance for vitamin $D_3$ formation and the effective irradiance for erythema formation R =$E_{pvD}/E_{er}$ under conditions of natural sunlight.

FIG. 2 shows spectra of simulated UV transmittances of four SPF 6 sunscreens (compositions in Table 1) with strong UVA (A1.3) and vitamin D3 optimized (A1.4) protective properties.

FIG. 3 shows spectra of simulated UV transmittances of four SPF 15 sunscreens (compositions in Table 2) with strong UVA (A2.3) and vitamin D3 optimized (A2.4) protective properties.

FIG. 4 shows spectra of simulated UV transmittances of four SPF 30 sunscreens (compositions in Table 3) with strong UVA (A3.3) and Vitamin D optimized (A3.4) protective properties.

The present invention relates to a method for increasing the transmittance of UV radiation for the production of cholecalciferol (vitamin $D_3$) on the human skin and simultaneously protecting the human skin against said UV radiation when exposed to the sun.

It is well known that chronic exposure to sunlight may have damaging effects to human skin. Depending on the wavelength UV radiation causes different types of skin damage. UV-B radiation (about 290 to about 320 nm) is responsible for sunburn and can cause skin cancer. UV-A radiation (about 320 to about 400 nm) while producing tanning of the skin contributes also to sunburn and the induction of skin cancers.

Nowadays it is well acknowledged that adequate sun protection should include broadband protection, that means, i.e. sunscreen should protect against both UVA and UVB radiation. Since 2006 the European Recommendation, requires a minimum UVA protection related to the level of UVB protection which implies that the UVA-PF (UVA protection factor) is at least ⅓ of the SPF (sun protection factor).

Apart from the known damaging effects of UV radiation a certain amount of UVB radiation is necessary for the formation of vitamin $D_3$ and its precursors in the skin.

By reducing the erythemally effective irradiance (=$E_r$) with sunscreens in order to prevent sunburn the effective irradiance responsible for vitamin $D_3$ formation (=$E_{pvD}$) is reduced as well. Thus, sunscreens can reduce or even prevent the vitamin $D_3$ production in skin. This is not surprising, because the radiation which is responsible for causing sunburn (erythema) and skin damage is in the same of radiation range which is also responsible for epidermal vitamin $D_3$ synthesis. It has been shown that topical application of a sunscreen with a sun protection factor of 8 prevented any increase in circulating concentrations of vitamin $D_3$ after a whole-body exposure to simulated sunlight that would have caused mild sunburn. Hence, the use of sunscreen can diminish the body's own production of vitamin $D_3$ and chronic sunscreen use can lead to unwanted lower vitamin $D_3$ levels in blood.

The problem underlying the present invention is to find sunscreens which counteract the inhibition of vitamin $D_3$ formation during sun exposure.

Surprisingly it was found that sunscreens comprising at least one specific UV filter will comply with these requirements.

Therefore, the present invention refers to a sunscreen formulation comprising at least one of the UV filters (A) selected from
(a) triazine derivatives;
(b) cinnamic acid derivatives;
(c) bis-resorcinyl triazines;
(f) benzimidazole derivatives;
($i_5$) 4-Methylbenzylidene Camphor;
(h) benzoyl piperazine derivatives;
(j) benzoxazole derivatives;
(k) diarylbutadiene derivatives;
(l) phenyl benzotriazole derivatives;
(n) benzylidene malonates;
($o_3$) TEA-Salicylate;
(r) imidazoline derivatives;
(u) inorganic UV filters selected from metal oxides;
(v) naphthalates; and
(w) merocyanine derivatives; and
optionally comprising at least one of the UV filters (B) selected from
(d) aminobenzophenone derivatives;
(e) dibenzoylmethane derivatives;
(g) β,β-Diphenylacrylate derivatives;
(i) camphor derivatives different from ($i_5$);
(o) salicylate derivatives different from ($o_3$);
(p) anthranilate derivatives; and
(s) benzalmalonate derivatives; wherein
  the ratio R of the effective irradiance for vitamin $D_3$ formation $E_{pvd}$ to the effective irradiance for erythema formation $E_{er}$ on the skin is at least 1.8,
for increasing the transmittance of UV radiation on human skin for the production of vitamin $D_3$ and simultaneously for the use in a method for protecting the human skin against UV radiation when exposed to the sun, which method comprises applying said sunscreen formulation to the skin.

Effective Irradiance

The effective irradiance $E_{er}$ can be calculated by multiplying the irradiance of the light source (=standard sun irradiance S(λ)) with the respective action spectrum $s_{er}(λ)$ for erythema formation and $S_{pvD}(λ)$ for vitamin $D_3$ production, respectively at any wavelength in a spectral range according to the following formulas:

($EI_{er}$): Effective irradiance $E_{er}$ for erythema formation $E_{er}=∫S(λ)s_{er}(λ)dλ$ ($EI_{pvD}$): Effective irradiance $E_{pvD}$ for vitamin $D_3$ formation: $E_{pvD}=∫S(λ)s_{VD}(λ)dλ$ The ratio of the effective irradiance for vitamin $D_3$ formation and the effective irradiance for erythema formation R=$E_{pvD}/E_{er}$ under conditions of natural sunlight is approximately $$R_{sun} = \frac{E_{pvD}}{E_{er}} \approx 2$$

This can be illustrated by FIG. 1:

The UV filter classes as defined in claim 1 comprise different kinds of UV filters, i.e. UV-B filters (290-320 nm), UV-AII filters (320-340 nm), and broad spectrum and UV-AI filters (340-400 nm).

In the following representatives of common UV filter classes are listed.

Suitable triazine derivatives (a) are selected from ($a_1$) Ethylhexyl Triazone;
($a_2$) Tris-Biphenyl Triazine;
($a_3$) Diethylhexyl Butamido Triazone,
($a_4$) Phenylene Bis-Diphenyltriazine;
($a_5$) 5,6,5',6'-tetraphenyl-3,3'-(1,4-Phenylene)bis(1,2,4-Triazine) corresponding to the formula

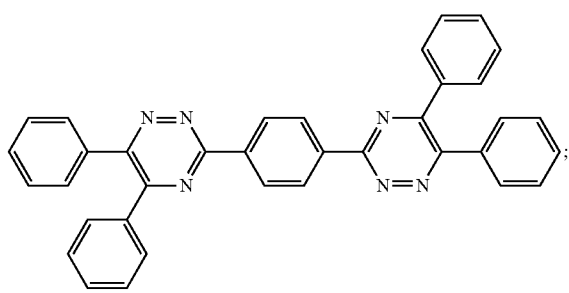

(TD1)

($a_6$) Benzoic acid, 4,4'-[[6-[[3-[1,3,3,3-tetramethyl-1-[(trimethylsilyl)oxy]-1-disiloxanyl]propyl]-amino]-1,3,5-triazine-2,4-diyl]diimino]bis-, dibutyl ester of formula

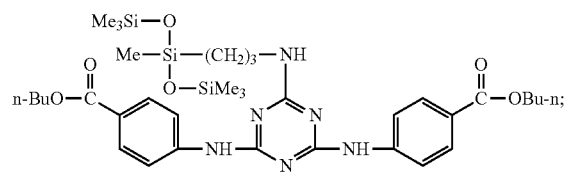

(TD1)

Suitable cinnamic acid derivatives (b) are selected from ($b_1$) Ethylhexyl Methoxy Cinnamate;
($b_2$) Isopropyl Methoxy Cinnamate;
($b_3$) Isoamyl Methoxy Cinnamate;
($b_4$) Diisopropyl Methyl Cinnamate,
($b_5$) Cinnoxate;
($b_6$) Glyceryl Ethylhexanoate,
($b_7$) 2-Propenoic acid, 3-(4-ethoxyphenyl)-, 2-methylphenyl ester of formula

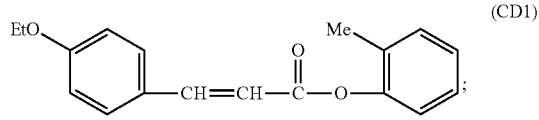 [SMILES: CCOc1ccc(C=CC(=O)Oc2ccccc2C)cc1]

(CD1)

($b_8$) 2-Propenoic acid, 3-(4-methoxyphenyl)-, 2-methylphenyl ester of formula

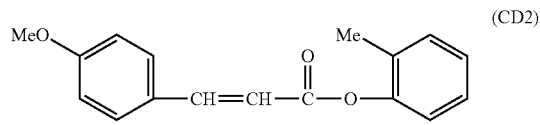 [SMILES: COc1ccc(C=CC(=O)Oc2ccccc2C)cc1]

(CD2)

($b_9$) Propanedioic acid, 2-[(4-methoxyphenyl)methylene]-, 1,3-bis(2-methylbutyl) ester of formula

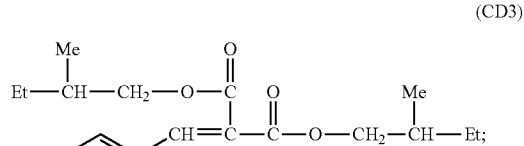

(CD3)

($b_{10}$) Propanedioic acid, 2-[(4-methoxyphenyl)methylene]-, 1,3-bis(2-ethylhexyl) ester of formula

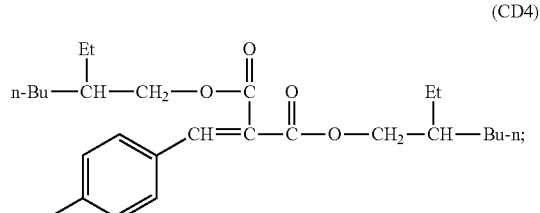

(CD4)

Suitable Bis-resorcinyl triazines (c) are selected from
($c_1$) Bis-Ethylhexyloxyphenol Methoxyphenyl Triazine; and
($c_2$) Aqueous dispersion of Bis-Ethylhexyloxyphenol Methoxyphenyl Triazine/Polymethyl Methacrylate.

Suitable aminobenzophenone derivatives (d) are selected from
($d_1$) Diethylamino Hydroxybenzoyl Hexyl Benzoate.

Suitable dibenzoylmethane derivatives (e) are selected from
($e_1$) Butyl Methoxy Dibenzoyl Methane; and
($e_2$) Isopropyl Dibenzoylmethane.

Suitable benzimidazole derivatives (f) are selected from
($f_1$) Phenyl Benzimidazole Sulfonic Acid; and
($f_2$) Disodium Phenyl Dibenzimidazole Tetrasulfonate.

Suitable β,β-Diphenylacrylate derivatives (g) are selected from
($g_1$) Octocrylene; and
($g_2$) Etocrylene.

Suitable benzoyl-piperazine derivatives (h) are selected from
($h_1$) 1,4-(2-(4-diethylamino-2-hydroxybenzoyl)benzoyl) piperazine.

Suitable camphor derivatives (i) are selected from
($i_1$) Terephthalylidene Dicamphor Sulfonic Acid;
($i_2$) Benzylidene Camphor Sulfonic Acid;
($i_3$) Camphor Benzalkonium Methosulfate;
($i_4$) 3-Benzylidene Camphor;
($i_5$) Methylbenzylidene Camphor; and
($i_6$) Polyacrylamidomethyl Benzylidene Camphor.

Suitable benzoxazole derivatives (j) are selected from
($j_1$) Ethylhexyl Bis-Isopentylbenzoxazolylphenyl Melamine.

Suitable diarylbutadiene derivatives (k) are selected from
($k_1$) 1,1-dicarboxy(2,2'-dimethyl-propyl)-4,4-diphenylbutadiene.

Suitable phenyl benzotriazole derivatives (l) are selected from
($l_1$) Methylene Bis-Benzotriazolyl Tetramethyl Butylphenol;
($l_2$) Drometrizole trisiloxane;
($l_3$) Phenol, 2-(2H-benzotriazol-2-yl)-6-[[(2-ethylhexyl)oxy]methyl]-4-methyl- of formula

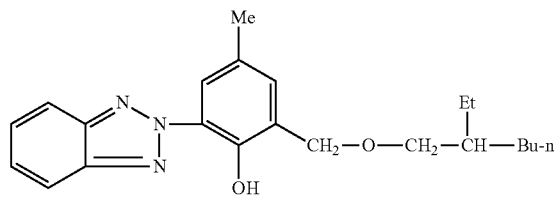

(PBT1)

($l_4$) Benzotriazolyl Dodecyl p-Cresol;
($l_5$) polymeric benzotriazole type UV filter as described in US 20110195036, WO 2011097555; e.g. a polymer prepd. from a dimer diol ($C_{36}H_{72}O$), ditrimethylolpropane, di-methyl adipate, methyl adipate, and methyl 3-(2H-benzotriazol-2-yl)-5-(1,1-dimethylethyl)-4-hydroxybenzenepropanoate; and
($l_6$) 2-(2H-Benzotriazol-2-yl)-6-(2-ethylhexyloxymethyl)-4-methyl-phenol corresponding to formula

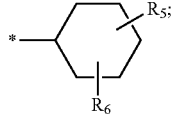

(PBT2)

Suitable malonic acid derivatives (n) are selected from
($n_1$) benzylidene malonates of formula

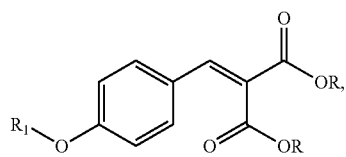

(BM)

wherein
$R_1$ is methyl; ethyl; propyl; or n-butyl;
if $R_1$ is methyl, then
R is tert. butyl;

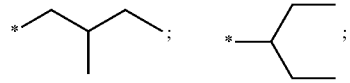

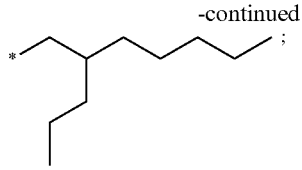

a radical of formula

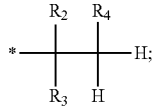

(BMa)

or a radical of formula

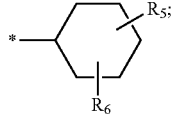

(BMb)

wherein
$R_2$ and $R_3$, independently from each other are hydrogen; or methyl;
$R_4$ is methyl; ethyl; or n-propyl;
$R_5$ and $R_6$ independently from each other are hydrogen; or $C_1$-$C_3$alkyl;
if $R_1$ is ethyl; propyl; or n-butyl, then
R is isopropyl.
Preferably, in formula (BM)
R is a radical of formula

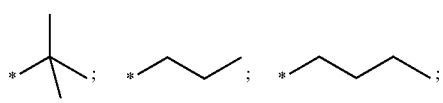

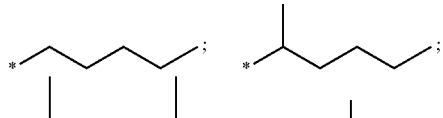

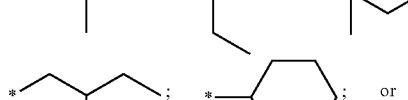

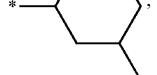

and
$R_1$ is methyl.

Most preferred is the compound of formula

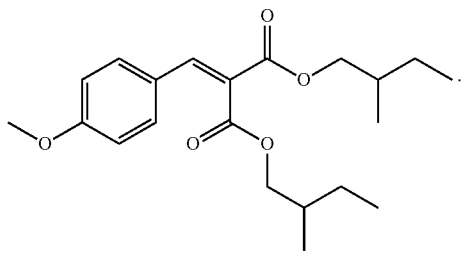
(BM9)

Examples of compounds of formula (BM) are listed in the Table 1 below:

TABLE 1

Examples of monomeric benzylidene malonates according to the present invention

| | $R_1$ | R |
|---|---|---|
| (BM1) | methyl | *–C(CH₃)₃ (tert-butyl) |
| (BM2) | methyl | *–propyl |
| (BM3) | methyl | *–pentyl |
| (BM4) | methyl | *–hexyl |
| (BM5) | methyl | *–2-methylpentyl |
| (BM6) | methyl | *–2-methylpropyl |
| (BM7) | methyl | *–3-methylpentyl |
| (BM8) | methyl | *–2,2-dimethylpropyl |
| (BM9) | methyl | *–2-methylbutyl |

TABLE 1-continued

Examples of monomeric benzylidene malonates according to the present invention

| | $R_1$ | R |
|---|---|---|
| (BM10) | ethyl | *–isopropyl |
| (BM11) | propyl | *–isopropyl |
| (BM12) | n-butyl | *–isopropyl |
| (BM13) | methyl | *–2-propylheptyl |

Further suitable malonates (n) refer to
($n_2$) Diethylhexyl Syringylidenemalonate corresponding to formula

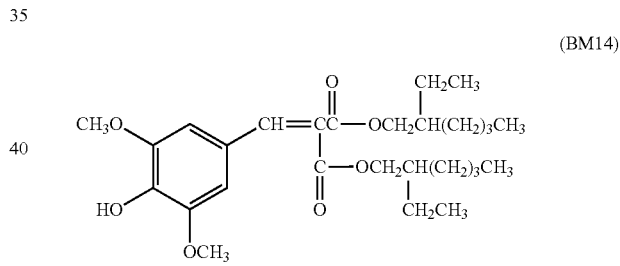
(BM14)

Suitable salicylate derivatives are selected from
($o_1$) Ethylhexyl Salicylate;
($o_2$) Dipropyleneglycol Salicylate;
($o_3$) TEA Salicylate; and
($o_4$) Homosalate
Suitable anthranilate derivatives (p) refer to
($p_1$) Menthyl Anthranilate.
Suitable imidazoline derivatives (r) are selected from
($r_1$) Ethylhexyl Dimethoxybenzylidene; and
($r_2$) Dioxoimidazoline Propionate.
Suitable benzamalonate derivatives are selected from
($s_1$) Polysilicone-15.
Suitable inorganic UV filters (u) are selected from
($u_1$) Zinc Oxide;
($u_2$) $Fe_2O_3$; and
($u_3$) Titanium Dioxide.
Suitable naphthalates (v) are selected from
($v_1$) Diethylhexyl 2,6-Naphthalate.
Preferably the sunscreen formulation according to the present invention has an SPF of at least 2.
More preferably the sunscreen formulation according to the present invention has an SPF of at least 6.

The sunscreen formulation according to the present invention comprises 1, or more than 1 UV filter.

For example, the sunscreen formulation according to the present invention may comprise 1, 2, 3, 4, 5 or 6 UV filters selected from the UV filter classes as defined in claim 1.

Preferably the sun screen formulation according to the present invention comprises the UV filters selected from
($a_1$) Ethylhexyl Triazone.
($a_2$) Tris-Bephenyl Triazine;
($a_3$) Diethylhexyl Butamido Triazone;
($c_1$) Bis-Ethylhexyloxyphenol Methoxyphenyl Triazine;
($c_2$) Aqueous dispersion of Bis-Ethylhexyloxyphenol Methoxyphenyl Triazine/Polymethyl Methacrylate;
($d_1$) Diethylamino Hydroxybenzoyl Hexyl Benzoate;
($e_1$) Butyl Methoxy Dibenzoyl Methane;
($f_1$) Phenyl Benzimidazole Sulfonic Acid;
($f_2$) Disodium Phenyl Dibenzimidazole Tetrasulfonate;
($g_1$) Octocrylene;
($h_1$) 1,4-(2-(4-diethylamino-2-hydroxybenzoyl)benzoyl) piperazine;
($l_1$) Methylene Bis-Benzotriazolyl Tetramethyl Butylphenol;
($l_2$) Drometrizole trisiloxane;
($l_6$) 2-(2H-Benzotriazol-2-yl)-6-(2-ethylhexyloxymethyl)-4-methyl-phenol;
($i_1$) Terephthalylidene Dicamphor Sulfonic Acid;
($n_1$) Compound of formula (BM9);
($o_1$) Ethylhexyl Salicylate;
($o_4$) Homosalate;
($p_1$) Menthyl Anthranilate;
($s_1$) Polysilicone-15;
($u_1$) Zinc Oxide; and
($u_3$) Titanium Dioxide;

More preferably the sun screen formulation according to the present invention comprises the UV filters selected from
($a_1$) Ethylhexyl Triazone;
($b_1$) Ethylhexyl Methoxy Cinnamate;
($c_1$) Bis-Ethylhexyloxyphenol Methoxyphenyl Triazine;
($d_1$) Diethylamino Hydroxybenzoyl Hexyl Benzoate;
($l_1$) Methylene Bis-Benzotriazolyl Tetramethyl Butylphenol;
($e_1$) Butyl Methoxy Dibenzoyl Methane;
($f_1$) Phenyl Benzimidazole Sulfonic Acid;
($g_1$) Octocrylene; and
($u_3$) Titanium Dioxide.

Preferably this sun screen formulation has an SPF of at least 6.

Even more preferably the sun screen formulation according to the present comprises the UV filters selected from
($b_1$) Ethylhexyl Methoxy Cinnamate;
($c_1$) Bis-Ethylhexyloxyphenol Methoxyphenyl Triazine;
($d_1$) Diethylamino Hydroxybenzoyl Hexyl Benzoate;
($l_1$) Methylene Bis-Benzotriazolyl Tetramethyl Butylphenol;
($e_1$) Butyl Methoxy Dibenzoyl Methane;
($f_1$) Phenyl Benzimidazole Sulfonic Acid; and
($g_1$) Octocrylene.

Preferably this sun screen formulation has an SPF of at least 6.

Furthermore, the sun screen formulation according to the present preferably comprises the UV filters selected from
($c_1$) Bis-Ethylhexyloxyphenol Methoxyphenyl Triazine;
($d_1$) Diethylamino Hydroxybenzoyl Hexyl Benzoate;
($l_1$) Methylene Bis-Benzotriazolyl Tetramethyl Butylphenol; and
($e_1$) Butyl Methoxy Dibenzoyl Methane.

Preferably this sun screen formulation has an SPF of at least 6.

Preferably, the sun screen formulation according to the present comprises the UV filter concentrations selected from
(a) 0.1-40% b.w. triazine derivatives;
(b) 0.1-30% b.w. cinnamic acid derivatives;
(c) 0.1-10% b.w. bis-resorcinyl triazines;
(f) 0.1-10% b.w. benzimidazole derivatives;
($i_5$) 0.1-10% b.w. 4-Methylbenzylidene Camphor;
(h) 0.1-10% b.w. benzoyl piperazine derivatives;
(j) 0.1-10% b.w. benzoxazole derivatives;
(k) 0.1-20% b.w. diarylbutadiene derivatives;
(l) 0.1-30% b.w. phenyl benzotriazole derivatives;
(n) 0.1-20% b.w. benzylidene malonates;
($o_3$) 0.1-15% b.w. TEA-Salicylate;
(r) 0.1-10% b.w. imidazoline derivatives;
(u) 0.1-50% b.w. inorganic UV filters selected from metal oxides;
(v) 0.1-20% b.w. naphthalates; and
(w) 0.1-20% b.w. merocyanine derivatives; and
optionally comprising at least one of the UV filters (B) selected from
(d) 0.1-20% b.w. aminobenzophenone derivatives;
(e) 0.1-5% b.w. dibenzoylmethane derivatives;
(g) 0.1-1% b.w. β,β-Diphenylacrylate derivatives;
(i) 0.1-10% b.w. camphor derivatives different from ($i_5$);
(o) 0.1-35% b.w. salicylate derivatives different from ($o_3$);
(p) 0.1-10% b.w. anthranilate derivatives; and
(s) 0.1-10% b.w. benzalmalonate derivatives.

More preferably, the sun screen formulation according to the present comprises the UV filter concentrations selected from
($a_1$) 1-3% b.w. Ethylhexyl Triazone;
($b_1$) 1-3.5% b.w. Ethylhexyl Methoxycinnamate;
($c_1$) 0.6-10% b.w. Bis-Ethylhexyloxyphenol Methoxyphenyl Triazine;
($d_1$) 0.8-10% b.w. Diethylamino Hydroxybenzoyl Hexyl Benzoate;
($e_1$) 2-3% b.w. Butyl Methoxydibenzoylmethane;
($f_1$) 2-3% b.w. Phenyl Benzimidazole Sulfonic Acid;
($g_1$) 2.0-2.5% b.w. Octocrylene;
($l_1$) 2-7.5% b.w. Methylene Bis-Benzotriazolyl Tetramethylbutylphenol; and
($u_3$) 3.0-3.5% b.w. Titanium Dioxide.

The sunscreen formulations according to the present invention achieve an SPF of >15 by the use of the UV filter combinations of
($d_1$) Diethylamino Hydroxybenzoyl Hexyl Benzoate;
($l_1$) Methylene Bis-benzotriazolyl Tetramethyl Butylphenol; and
($e_1$) Butyl Methoxy Dibenzoyl Methane; most preferably
($d_1$) 9.0-11.0% b.w. of Diethylamino Hydroxybenzoyl Hexyl Benzoate;
($l_1$) 2.5-3.5% b.w. of Methylene Bis-Benzotriazolyl Tetramethylbutylphenol; and
($e_1$) 2.5-3.5% b.w Butyl Methoxydibenzoylmethane.

The sunscreen formulations according to the present invention achieve an SPF of >30 by the use of the UV filter combinations of
($c_1$) Bis-Ethylhexyloxyphenol Methoxyphenyl Triazine;
($d_1$) Diethylamino Hydroxybenzoyl Hexyl Benzoate;
($l_1$) Methylene Bis-Benzotriazolyl Tetramethyl Butylphenol; and
($e_1$) Butyl Methoxy Dibenzoyl Methane;
most preferably
($c_1$) 1.5-2.5% b.w. of Bis-Ethylhexyloxyphenol Methoxyphenyl Triazine;
($d_1$) 9.5-10.5% b.w. of Diethylamino Hydroxybenzoyl Hexyl Benzoate;
($l_1$) 7-8% b.w. of Methylene Bis-Benzotriazolyl Tetramethylbutylphenol; and ($e_1$) 2.5-3.5% b.w. of Butyl Methoxydibenzoylmethane.

Preferably sunscreen formulation according to the present invention are used, wherein the UV filters are selected from the broadband (spectrum of 340 to 400 nm) UV filters
($c_1$) Bis-Ethylhexyloxyphenol Methoxyphenyl Triazine;
($c_2$) Aqueous dispersion of Bis-Ethylhexyloxyphenol Methoxyphenyl Triazine/Polymethyl Methacrylate;
($f_2$) Disodium Phenyl Dibenzimidazole Tetrasulfonate;
($l_1$) Methylene Bis-Benzotriazolyl Tetramethyl Butylphenol;
($l_2$) Drometrizole trisiloxane;
($u_1$) Zinc Oxide; and optionally
($e_1$) Butyl Methoxy Dibenzoyl Methane;
($d_1$) Diethylamino Hydroxybenzoyl Hexyl Benzoate;
($i_1$) Terephthalylidene Dicamphor Sulfonic Acid; and
($p_1$) Menthyl Anthranilate.

Furthermore, the present invention refers to sunscreen formulations comprising a UV filter selected from
(a) triazine derivatives
(b) cinnamic acid derivatives;
(c) bis-resorcinyl triazines;
(f) benzimidazole derivatives;
(h) benzoyl-piperazine derivatives;
($i_5$) 4-Methylbenzylidene Camphor;
(l) phenyl benzotriazole derivatives;
(n) benzylidene malonates;
($o_3$) TEA-Salicylate;
(r) imidazoline derivatives;
(u) inorganic UV filters selected from metal oxides;
(v) naphthalates; and
(w) merocyanine derivatives;
wherein the sunscreen formulation contains only one of the selected UV filters.

Preferably sunscreen formulations are used, wherein the UV filters are selected from broadband
(spectrum of 340 to 400 nm) UV filters
($c_1$) Bis-Ethylhexyloxyphenol Methoxyphenyl Triazine;
($c_2$) Aqueous dispersion of Bis-Ethylhexyloxyphenol Methoxyphenyl Triazine/Polymethyl Methacrylate;
($f_2$) Disodium Phenyl Dibenzimidazole Tetrasulfonate;
($l_1$) Methylene Bis-Benzotriazolyl Tetramethyl Butylphenol;
($i_1$) Terephthalylidene Dicamphor Sulfonic Acid; and
($u_1$) Zinc Oxide;
wherein the sunscreen formulation contains only one of the selected UV filters.

Furthermore, sunscreen formulations are preferred, which comprise particulate UV filters selected from
($a_2$) Tris-Bephenyl Triazine;
($c_2$) Aqueous dispersion of Bis-Ethylhexyloxyphenol Methoxyphenyl Triazine/Polymethyl Methacrylate;
($h_1$) 1,4-(2-(4-diethylamino-2-hydroxybenzoyl)benzoyl)piperazine;
($l_1$) Methylene Bis-Benzotriazolyl Tetramethyl Butylphenol;
($u_1$) Zinc Oxide; and
($u_3$) Titanium Dioxide.

Furthermore, sunscreen formulations are preferred, which comprise non-particulate UV filters selected from
($a_1$) Ethylhexyl Triazone.
($a_3$) Diethylhexyl Butamido Triazone;
($c_1$) Bis-Ethylhexyloxyphenol Methoxyphenyl Triazine;
($d_1$) Diethylamino Hydroxybenzoyl Hexyl Benzoate;
($e_1$) Butyl Methoxy Dibenzoyl Methane;
($f_1$) Phenyl Benzimidazole Sulfonic Acid;
($f_2$) Disodium Phenyl Dibenzimidazole Tetrasulfonate;
($g_1$) Octocrylene;
($h_1$) 1,4-(2-(4-diethylamino-2-hydroxybenzoyl)benzoyl)piperazine;
($l_1$) Methylene Bis-Benzotriazolyl Tetramethyl Butylphenol;
($l_2$) Drometrizole trisiloxane;
($l_6$) 2-(2H-Benzotriazol-2-yl)-6-(2-ethylhexyloxymethyl)-4-methyl-phenol;
($i_1$) Terephthalylidene Dicamphor Sulfonic Acid;
($n_1$) Compound of formula (BM9);
($o_1$) Ethylhexyl Salicylate;
($o_4$) Homosalate;
($p_1$) Menthyl Anthranilate; and
($s_1$) Polysilicone-15.

The preferred ratio of the effective irradiance for vitamin $D_3$ formation $E_{pvd}$ to the effective irradiance for erythema formation $E_{er}$ on the skin of the sunscreen formulations according to the present invention wherein is at least 1.8, preferably at least 1.85, more preferably at least 1.90 even more preferably >1.95, most preferably at least 2.0 and upmost preferably at least 2.1.

Further sunscreen formulations according to the present invention wherein the ratio of the effective irradiance for vitamin $D_3$ formation $E_{pvd}$ to the effective irradiance for erythema formation $E_{er}$ on the skin is at least 1.8; and which contain the UV filter combinations CSF 1-CSF 32 of Table 1 are preferred.

TABLE 1

UV filter combinations according to the present invention a

| UV filter | CSF 1 | CSF 2 | CSF 3 | CSF 4 | CSF 5 | CSF 6 | CSF 7 | CSF 8 | CSF 9 | CSF 10 | CSF 11 | CSF 12 | CSF 13 | CSF 14 | CSF 15 | CSF 16 | CSF 17 |
|---|---|---|---|---|---|---|---|---|---|---|---|---|---|---|---|---|---|
| ($a_1$) |  | X | X |  |  |  |  |  |  |  |  |  |  |  |  |  |  |
| ($a_2$) |  |  |  | X |  |  |  |  |  |  |  |  |  |  |  |  |  |
| ($a_3$) |  |  |  |  |  |  |  |  |  |  |  |  |  |  |  |  |  |
| ($c_1$) | X | X | X |  |  |  |  | X | X |  |  |  |  | X | X | X | X |
| ($c_2$) |  | X | X |  |  |  |  |  |  |  |  |  |  |  |  |  |  |
| ($d_1$) |  | X | X |  |  |  | X |  |  |  |  |  |  |  |  |  |  |
| ($e_1$) | X |  |  |  |  |  |  |  |  |  |  |  |  |  |  |  | X |
| ($f_1$) |  |  | X |  |  |  |  |  |  |  |  |  |  |  |  |  |  |
| ($g_1$) |  |  |  |  |  |  |  |  |  |  |  |  |  |  |  |  | X |
| ($h_1$) | X | X | X |  | X |  | X |  | X | X |  |  | X |  |  | X | X |
| ($i_1$) |  |  |  |  |  |  |  | X |  |  |  |  | X |  |  |  | X |
| ($l_1$) | X |  |  | X | X | X | X | X |  |  | X | X |  |  |  |  |  |
| ($l_2$) |  |  |  |  |  |  |  |  |  |  |  |  |  |  |  |  |  |
| (m) |  |  |  |  |  |  |  |  |  |  |  |  |  |  |  |  |  |
| ($n_1$) |  |  |  |  |  |  |  |  |  |  |  |  |  |  |  |  |  |
| ($o_1$) |  |  |  |  |  |  |  |  |  |  |  |  |  |  |  |  |  |

TABLE 1-continued

UV filter combinations according to the present invention

| | CSF 18 | CSF 19 | CSF 20 | CSF 21 | CSF 22 | CSF 23 | CSF 24 | CSF 25 | CSF 26 | CSF 27 | CSF 28 | CSF 29 | CSF 30 | CSF 31 |
|---|---|---|---|---|---|---|---|---|---|---|---|---|---|---|
| ($u_1$) | | | | | X | | | | | X | X | X | | |
| ($u_3$) | | | | | | | X | X | X | X | X | | | |
| ($l_6$) | | | | | | X | X | X | X | X | | | | | b

| UV filter | CSF 18 | CSF 19 | CSF 20 | CSF 21 | CSF 22 | CSF 23 | CSF 24 | CSF 25 | CSF 26 | CSF 27 | CSF 28 | CSF 29 | CSF 30 | CSF 31 |
|---|---|---|---|---|---|---|---|---|---|---|---|---|---|---|
| ($a_1$) | | | | | | | | | | | | | X | |
| ($a_2$) | | | | | | | | | | | | | | X |
| ($a_3$) | | X | | | | | | | | | | | | |
| ($c_1$) | X | X | | X | | X | X | X | X | | X | X | X | |
| ($c_2$) | | | | | | | | | | | | | | |
| ($d_1$) | | | | | | | | | | | | | | |
| ($e_1$) | | | | | | X | X | X | X | X | X | X | X | |
| ($f_1$) | | | | | | | | | | | | | | |
| ($f_2$) | X | X | | | | | | | | | | | | |
| ($g_1$) | | | | | | | | | | X | | | | |
| ($h_1$) | | | X | | | X | X | X | X | | X | X | X | |
| ($i_1$) | | | | | | | | | | | X | X | X | |
| ($l_1$) | | | X | | | X | X | X | X | | | | | X |
| ($l_2$) | | | | | | | | | | | | | | |
| (m) | | | | | | | | | | | | | | |
| ($n_1$) | | | | | | | | | | | X | X | | |
| ($o_1$) | | | | | | X | X | | | | | | | |
| ($o_4$) | | | | | | | | | X | | | | | |
| ($p_1$) | | | | | | | | | | | X | | | |
| ($s_1$) | X | | | | | | | | | | | | | |
| (u1) | | X | X | X | | | | | | | | | | |
| (u3) | | X | | | X | X | X | X | | | | | | X |

According to the present invention sunscreen compositions with optimized transparency for improved vitamin $D_3$ production in a huge range of SPFs up to >SPF60 can be provided, which include but are not limited to the sun protection factors (abbreviated as SPF) proposed by the European Commission Recommendation: SPF 6, 15, 30, 50 and 50+(>60). According to the EC Recommendation an SPF of 6 belongs to the class of "low protection", an SPF 15 to the "medium protection", an SPF 30 and 50 to the "high protection", and SPF 50+ (requiring SPF min 60) to the "very high protection" category.

Regarding broadband protection the EC recommendation says that the ratio of UVA-PF/SPF should at least be 1/3, and the critical wavelength (CW) at least 370 nm. For low UVA protection the UVA-PF/SPF ratio is significantly lower, for high UVA-protection, it is far higher than 1/3.

Sunscreens necessarily reduce both $E_{er}$ and $E_{pvd}$ on the skin. The ratio $R=E_{pvd}/E_{er}$ can be optimized by choosing an adequate UV filter combination. The higher the said ratio R, the better the sunscreen will perform concerning the vitamin $D_3$ production for a given protection against $E_{er}$.

The sun screen formulation according to the present invention is especially useful for the protection of organic materials that are sensitive to ultraviolet light, especially human and animal skin and hair, against the action of UV radiation and simultaneously for increasing the transmittance of UV radiation for the production of vitamin $D_3$ on the human ski. Such UV filter combinations are therefore suitable as light-protective agents in cosmetic and pharmaceutical preparations.

The sun screen formulations according to the present invention contain from 1 to 50% by weight, preferably 1-20% by weight, preferably from 3 to 15% by weight, based on the total weight of the formulation, the combination of UV filters as defined in claim 1 and a cosmetically tolerable adjuvant The sun screen formulations according to the present invention can be prepared by physically mixing the UV filters as defined in claim 1 with the adjuvant using customary methods, for example by simply stirring together the individual components, especially by making use of the dissolution properties of already known cosmetic UV absorbers, for example Ethylhexyl Methoxycinnamate (UV filter component ($b_1$)). The UV filters as defined in claim 1 can be used in the sunscreen formulation, for example, without further treatment.

Some of the UV filters used in the sunscreen of the present invention, for example ($l_1$) Methylene Bis-Benzotriazolyl Tetramethylbutylphenol, ($a_2$) Tris-Biphenyl Triazine or ($h_1$) 1,4-(2-(4-diethylamino-2-hydroxybenzoyl)benzoyl)piperazine cane used in their micronized state (nanoscalar organic filters, particulate organic filters, UV-absorber pigments).

Any known process suitable for the preparation of microparticles can be used for the preparation of the micronised UV filters, for example wet-milling (low viscous micronization process for pumpable dispersions), with a hard grinding medium, for example zirconium silicate balls in a ball mill and a protective surfactant or a protective polymer in water or in a suitable organic solvent, wet-kneading (high viscous micronization process non pumpable pastes) using a continuous or discontinuous (batch) kneader, spray-drying from a suitable solvent, by the expansion according to the RESS process (Rapid Expansion of Supercritical Solutions) of supercritical fluids (e.g. $CO_2$), or by precipitation from suitable solvents, including supercritical fluids.

Suitable milling apparatus for the preparation of the micronized organic UV filters are for example, a jet mill, ball mill, vibratory mill or hammer mill, preferably a high-speed mixing mill or ball mills. The grinding is preferably carried out with a grinding aid.

The micronized UV filters so obtained usually have an average particle size from 0.02 to 2 micrometer, preferably from 0.05 to 1.5 micrometer and more especially from 0.1 to 1.0 micrometer.

The micronized UV filters used in the present invention are preferably present as aqueous dispersions. The grinding of the sparingly soluble organic compounds used in the present invention is preferably carried out with a grinding aid. The dispersing agent is used as a low molecular weight grinding aid for all the above micronisation processes. Preferred useful grinding aids for an aqueous dispersion are anionic surfactants with a HLB value higher than 8, more preferably higher than 10. Any conventionally usable anionic, non-ionic or amphoteric surfactants can be used as dispersing agents (component (b)). Such surfactant systems may comprise for example: carboxylic acids and their salts: alkaline soap of sodium, potassium and ammonium, metallic soap of calcium or magnesium, organic basis soap such as Lauric, myristic, palmitic, stearic and oleic acid etc. . . . . Alkyl phosphates or phosphoric acid esters, acid phosphate, diethanolamine phosphate, potassium cetyl phosphate. Ethoxylated carboxylic acids or polyethyleneglycol esters, PEG-n acylates. Fatty alcohol polyglycolether such as laureth-n, myreth-n, ceteareth-n, steareth-n, oleth-n. Fatty acid polyglycolether such as PEG-n-stearate, PEG-n oleate, PEG-n cocoate. Monoglycerides and polyol esters. C12-C22 fatty acid mono- and di-esters of addition products of from 1 to 100 mol of ethylene oxide with polyols. Fatty acid and polyglycerol ester such as monostearate glycerol, diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable. Fatty acid polyglycolesters such as monostearate diethylene glycol, fatty acid and polyethylene glycol esters, fatty acid and saccharose esters such as sucre esters, glycerol and saccharose esters such as sucre glycerides. Sorbitol and sorbitan, sorbitan mono- and di-esters of saturated and unsaturated fatty acids having from 6 to 22 carbon atoms and ethylene oxide addition products. Polysorbate-n series, sorbitan esters such as sesquiisostearate, sorbitan, PEG(6)isostearate sorbitan, PEG-(10)-sorbitan laurate, PEG-17-dioleate sorbitan. Glucose derivatives, C8-C22 alkyl-mono and oligo-glycosides and ethoxylated analogues with glucose being preferred as the sugar component. 0/W emulsifiers such as methyl gluceth-sesquistearate, sorbitan stearate/sucrose cocoate, methyl glucose sesquistearate, cetearyl alcohol/cetearyl glucoside. W/0 emulsifiers such as methyl glucose dioleate/methyl glucose isostearate. Sulfates and sulfonated derivatives, dialkylsulfosuccinates, dioctyl succinate, alkyllauryl sulfonate, linear sulfonated parafins, sulfonated tetraproplyne sulfonate, sodium lauryl sulfates, ammonium and ethanolamine lauryl sulfates, lauyl ether sulfates, sodium laureth sulfates or sodium myreth sulfates, sulfosuccinates, aceyl isothionates, alkanolamide sulfates, taurines, methyl taurines, imidazole sulfates. Zwitterionic or amphoteric surfactants that carry at least one quaternary ammonium group and at least one carboxylate and/or sulfonate group in the molecule. Zwitterionic surfactants that are especially suitable are betaines, such as N-alkyi-N, N-dimethylammonium glycinates, cocoalkyldimethylammonium glycinate, N-acylaminopropyi-N,N-dimethylammonium glycinates, cocoacylaminopropyldimethylammonium glycinate and 2-alkyl-3-carboxymethyl-3-hydroxyethylimidazolines each having from 8 to 18 carbon atoms in the alkyl or acyl group and also cocoacylaminoethylhydroxyethylcarboxymethylglycinate, N-alkylbetaine, Nalkylaminobetaines. Examples of suitable mild surfactants as dispersing agents, that is to say surfactants especially well tolerated by the skin, include fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, a.-olefin sulfonates, ethercarboxylic acids, alkyl oligoglucosides, fatty acid glucamides, alkylamidobetaines and/or protein fatty acid condensation products, the latter preferably being based on wheat proteins. Non ionic surfactants such as PEG-6 beeswax (and) PEG-6 stearate (and) polyglyceryl-2-isostearate [Apifac], glyceryl stearate (and) PEG-1 00 stearate. [Arlacel 165], PEG-5 glyceryl stearate (arlatone 983 S], sorbitan oleate (and) polyglyceryl-3 ricinoleate. [Arlacel 1689), sorbitan stearate and sucrose cocoate [arlatone 2121], glyceryl stearate and laureth-23 [Cerasynth 945], cetearyl alcohol and ceteth-20 [Cetomacrogol Wax], cetearyl alcohol and colysorbate 60 and PEG-150 and stearate-20[Polawax GP 200, Polawax NF], cetearyl alcohol and cetearyl polyglucoside [Emulgade PL 1618], cetearyl alcohol and ceteareth-20 [Emulgade 1 OOONI, Cosmowax]. cetearyl alcohol and PEG-40 castor oil [Emulgade F Special], cetearyl alcohol and PEG-40 castor oil and sodium cetearyl sulfate [Emulgade F], stearyl alcohol and steareth-7 and steareth-10 [Emulgator E 2155], cetearyl alcohol and szeareth-7 and steareth-10 [Emulsifying wax U.S.N.F], glyceryl stearate and PEG-75 stearate [Gelot 64], propylene glycol ceteth-3 acetate. [Hetester PCS), propylene glycol-8-isoceth-3 acetate [Hetester PHA], cetearyl alcohol and ceteth-12 and oleth-12 [Lanbritol Wax N 21], PEG-6 stearate and PEG-32 stearate [Tefose 1500], PEG-6 stearate and ceteth-20 and steareth-20 [Tefose 2000], PEG-6 stearate and ceteth-20 and glyceryl stearate and steareth-20 [Tefose 2561], glyceryl stearate and ceteareth-20 [Teginacid H, C, X]. Anionic emulsifiers such as PEG-2 stearate SE, glyceryl stearate SE [Monelgine, Cutina KD], propylene glycol stearate [Tegin P], cetearyl Alcohol and Sodium cetearyl sulfate [Lanette N, Cutina LE, Crodacol GP], cetearyl alcohol and sodium lauryl sulfate [Lanette W], trilaneth-4 phopshate and glycol stearate and PEG-2 stearate [Sedefos 75], glyceryl stearate and sodium lauryl Sulfate [Teginacid Special]. Cationic acid bases such as cetearyl alcohol and cetrimonium bromide. Most preferred dispersing agents (b) are sodium alkyl sulfates or sodium alkyl ether sulfates, such as sodium laureth sulfate [Texapon N70 from Cognis] or sodium myreth sulfate [Texapon K14 S from Cognis]. The specific dispersing agents may be used in an amount of, for example, from 1 to 30% by weight, especially from 2 to 20% by weight and preferably from 3 to 10% by weight, based on the total weight of the composition. Useful solvents are water, brine, (poly)ethylene glycol, glycerol or cosmetically acceptable oils. Other useful solvents are disclosed below in the sections entitled "Esters of fatty acids", "Natural and synthetic triglycerides, including glyceryl esters and derivatives", "Pearlescent waxes", "Hydrocarbon oils" and "Silicones or siloxanes".

If the formulations according to the present invention represent water- and oil-containing emulsions (e.g. W/O, O/W, O/W/O and W/O/W emulsions or microemulsions) they contain, for example, from 0.1 to 30% by weight, preferably from 0.1 to 15% by weight and especially from 0.5 to 10% by weight, based on the total weight of the composition, of the UV filters selected from (a)-(x), from 1 to 60% by weight, especially from 5 to 50% by weight and preferably from 10 to 35% by weight, based on the total weight of the composition, of at least one oil component, from 0 to 30% by weight, especially from 1 to 30% by weight and preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically tolerable adjuvants.

Suitable oil components of oil-containing compositions (e.g. oils, W/O, O/W, O/W/O and W/O/W emulsions or microemulsions) are for example Guerbet alcohols based on fatty alcohols having from 6 to 18, preferably from 8 to 10, carbon atoms, esters of linear $C_6$-$C_{24}$ fatty acids with linear $C_3$-$C_{24}$ alcohols, esters of branched $C_6$-$C_{13}$ carboxylic acids with linear $C_6$-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, triglycerides based on $C_6$-$C_{10}$ fatty acids, liquid mono-/di-/tri-glyceride mixtures based on $C_6$-$C_{18}$ fatty acids, esters of $C_6$-$C_{24}$ fatty alcohols and/or Guerbet alcohols with aromatic carboxylic acids, especially benzoic acid, esters of $C_2$-$C_{12}$ dicarboxylic acids with linear or branched alcohols having from 1 to 22 carbon atoms or polyols having from 2 to 10 carbon atoms and from 2 to 6 hydroxy groups, vegetable oils (such as sunflower oil, olive oil, soybean oil, rapeseed oil, almond oil, jojoba oil, orange oil, wheat germ oil, peach kernel oil and the liquid components of coconut oil), branched primary alcohols, substituted cyclohexanes, linear and branched $C_6$-$C_{22}$ fatty alcohol carbonates, Guerbet carbonates, esters of benzoic acid with linear and/or branched $C_6$-$C_{22}$ alcohols (e.g. Finsolv® TN), linear or branched, symmetric or asymmetric dialkyl ethers having a total of from 12 to 36 carbon atoms, especially from 12 to 24 carbon atoms, for example di-n-octyl ether, di-n-decyl ether, di-n-nonyl ether, di-n-undecyl ether, di-n-dodecyl ether, n-hexyl n-octyl ether, n-octyl n-decyl ether, n-decyl n-undecyl ether, n-undecyl n-dodecyl ether, n-hexyl n-undecyl ether, di-tertbutyl ether, diisopentyl ether, di-3-ethyldecyl ether, tert-butyl n-octyl ether, isopentyl n-octyl ether and 2-methyl pentyl-n-octyl ether; ring-opening products of epoxidized fatty acid esters with polyols, silicone oils and/or aliphatic or naphthenic hydrocarbons. Also of importance are monoesters of fatty acids with alcohols having from 3 to 24 carbon atoms. That group of substances comprises the esterification products of fatty acids having from 8 to 24 carbon atoms, for example caproic acid, caprylic acid, 2-ethylhexanoic acid, capric acid, lauric acid, isotride-canoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerisation of unsaturated fatty acids) with alcohols, for example isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerisation of unsaturated fatty alcohols). Of special importance are isopropyl myristate, isononanoic acid $C_{16}$-$C_{18}$alkyl esters, stearic acid 2-ethylhexyl ester, cetyl oleate, glycerol tricaprylate, coconut fatty alcohol caprinate/caprylate and n-butyl stearate. Further oil components that can be used are dicarboxylic acid esters, such as di-n-butyl adipate, di(2-ethylhexyl) adipate, di(2-ethylhexyl) succinate and diisotridecyl acetate, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate. Preferred mono- or poly-ols are ethanol, isopropanol, propylene glycol, hexylene glycol, glycerol and sorbitol. It is also possible to use di- and/or trivalent metal salts (alkaline earth metal, $Al^{3+}$ inter alia) of one or more alkyl carboxylic acids.

The oil components can be used in an amount of, for example, from 1 to 60% by weight, especially from 5 to 50% by weight and preferably from 10 to 35% by weight, based on the total weight of the composition Any conventionally usable emulsifier can be used for the cosmetic compositions according to the present invention.

Suitable emulsifiers are for example, non-ionic surfactants from the following groups:

addition products of from 2 to 30 mol of ethylene oxide and/or from 0 to 5 mol of propylene oxide with linear fatty alcohols having from 8 to 22 carbon atoms, with fatty acids having from 12 to 22 carbon atoms and with alkylphenols having from 8 to 15 carbon atoms in the alkyl group, for example ceteareth-20 or ceteareth-12;

$C_{12}$-$C_{22}$ fatty acid mono- and di-esters of addition products of from 1 to 30 mol of ethylene oxide with polyols having from 3 to 6 carbon atoms, especially with glycerol;

glycerol mono- and di-esters and sorbitan mono- and di-esters of saturated and unsaturated fatty acids having from 6 to 22 carbon atoms and ethylene oxide addition products thereof, for example glyceryl stearates, glyceryl isostearates, glyceryl oleates, sorbitan oleates or sorbitan sesquioleates;

$C_8$-$C_{22}$alkyl-mono- and -oligo-glycosides and ethoxylated analogues thereof, degrees of oligomerisation of from 1.1 to 5, especially from 1.2 to 1.4, being preferred, and glucose being preferred as the sugar component;

addition products of from 2 to 60 mol, especially from 15 to 60 mol, of ethylene oxide with castor oil and/or hydrogenated castor oil;

polyol esters and especially polyglycerol esters, for example diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable;

partial esters based on linear, branched, unsaturated or saturated $C_6$-$C_{22}$ fatty acids, ricinoleic acid and also 12-hydroxystearic acid and on glycerol, polyglycerol, pentaerythritol, dipentaerythritol, sugar alcohols (e.g. sorbitol), alkyl glucosides (e.g. methyl glucoside, butyl glucoside, lauryl glucoside) and also polyglucosides (e.g. cellulose), for example polyglyceryl-2-dihydroxystearates or polyglyceryl-2-diricinoleates;

mono-, di- and tri-alkylphosphates and also mono-, di- and/or tri-PEG-alkylphosphates and salts thereof;

wool wax alcohols;

one or more ethoxylated esters of natural derivatives, for example polyethoxylated esters of hydrogenated castor oil;

silicone oil emulsifiers, for example silicone polyol;

polysiloxane/polyalkyl/polyether copolymers and corresponding derivatives, for example cetyl dimethicone copolyol;

mixed esters of pentaerythritol, fatty acids, citric acid and fatty alcohol (see DE-A-1 165 574) and/or mixed esters of fatty acids having from 6 to 22 carbon atoms, methylglucose and polyols, preferably glycerol or polyglycerol, for example polyglyceryl-3-glucose distearates, polyglyceryl-3-glucose dioleates, methyl glucose dioleates or dicocoyl pentaerythryl distearyl citrates; and also polyalkylene glycols.

The addition products of ethylene oxide and/or of propylene oxide with fatty alcohols, fatty acids, alkylphenols, glycerol mono- and di-esters and also sorbitan mono- and di-esters of fatty acids, or with castor oil, are known, commercially available products. They are usually homologue mixtures, the average degree of alkoxylation of which corresponds to the ratio of the amounts of ethylene oxide and/or propylene oxide and substrate with which the addition reaction is carried out. $C_{12}$-$C_{18}$ fatty acid mono- and di-esters of addition products of ethylene oxide with glycerol are known, for example, from DE-A-2 024 051 as fat-restoring substances for cosmetic preparations.

$C_8$-$C_{18}$Alkyl-mono- and -oligo-glycosides, their preparation and their use are known from the prior art. They are prepared especially by reacting glucose or oligosaccharides with primary alcohols having from 8 to 18 carbon atoms. Suitable glycoside radicals include monoglycosides in which a cyclic sugar radical is glycosidically bonded to the fatty alcohol and also oligomeric glycosides having a degree of oligomerisation of up to preferably about 8. The degree of oligomerisation is a statistical average value based on a homologue distribution customary for such technical-grade products.

It is also possible to use zwitterionic surfactants as emulsifiers. The term "zwitterionic surfactants" denotes especially surface-active compounds that carry at least one quaternary ammonium group and at least one carboxylate and/or sulfonate group in the molecule. Zwitterionic surfactants that are especially suitable are the so-called betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines each having from 8 to 18 carbon atoms in the alkyl or acyl group and also cocoacylaminoethylhydroxyethylcarboxymethylglycinate. Special preference is given to the fatty acid amide derivative known by the CTFA name cocamidopropyl betaine. Likewise suitable as emulsifiers are ampholytic surfactants. Ampholytic surfactants are to be understood as meaning especially those which, in addition to containing a $C_8$-$C_{18}$-alkyl or -acyl group, contain at least one free amino group and at least one —COOH or —SO$_3$H group in the molecule and are capable of forming internal salts. Examples of suitable ampholytic surfactants include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each having approximately from 8 to 18 carbon atoms in the alkyl group.

Ampholytic surfactants to which special preference is given are N-cocoalkylamino-propionate, cocoacylaminoethylaminopropionate and $C_{12}$-$C_{18}$acylsarcosine. In addition to the ampholytic emulsifiers there also come into consideration quaternary emulsifiers, special preference is given to those of the esterquat type, preferably methyl-quaternised di-fatty acid triethanolamine ester salts.

Non-ionic emulsifiers are preferred, preferably ethoxylated fatty alcohols having from 8 to 22 carbon atoms and from 4 to 30 EO units.

The emulsifiers may be used in an amount of, for example, from 1 to 30% by weight, especially from 4 to 20% by weight and preferably from 5 to 10% by weight, based on the total weight of the composition. It is, however, also possible in principle to dispense with the use of emulsifiers.

The compositions according to the invention, for example creams, gels, lotions, alcoholic and aqueous/alcoholic solutions, emulsions, wax/fat compositions, stick preparations, powders or ointments, may in addition contain, as further adjuvants and additives, mild surfactants, super-fatting agents, pearlescent waxes, consistency regulators, thickeners, polymers, silicone compounds, fats, waxes, stabilisers, biogenic active ingredients, deodorising active ingredients, antidandruff agents, film formers, swelling agents, antioxidants, hydrotropic agents, preservatives, insect repellents, self-tanning agents, solubilizers, perfume oils, colorants, bacteria-inhibiting agents and the like.

Substances suitable for use as super-fatting agents are, for example, lanolin and lecithin and also polyethoxylated or acrylated lanolin and lecithin derivatives, polyol fatty acid esters, monoglycerides and fatty acid alkanolamides, the latter simultaneously acting as foam stabilisers.

Examples of suitable mild surfactants, that is to say surfactants especially well tolerated by the skin, include fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines and/or protein fatty acid condensation products, the latter preferably being based on wheat proteins.

Suitable pearlescent are for example: alkylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially laurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

Suitable consistency regulators are especially fatty alcohols or hydroxy fatty alcohols having from 12 to 22 carbon atoms and preferably from 16 to 18 carbon atoms, and in addition partial glycerides, fatty acids and hydroxy fatty acids. Preference is given to a combination of such substances with alkyl-oligoglucosides and/or fatty acid N-methylglucamides of identical chain length and/or polyglycerol poly-12-hydroxystearates. Suitable thickeners include, for example, Aerosil types (hydrophilic silicic acids), polysaccharides, especially xanthan gum, guar-guar, agar-agar, alginates and Tyloses, carboxymethyl cellulose and hydroxymethyl cellulose, also relatively high molecular weight polyethylene glycol mono- and di-esters of fatty acids, polyacrylates (e.g. Carbopol® from Goodrich or Synthalen® from Sigma), polyacrylamides, polyvinyl alcohol and polyvinylpyrrolidone, surfactants, for example ethoxylated fatty acid glycerides, esters of fatty acids with polyols, for example pentaerythritol or trimethylolpropane, fatty alcohol ethoxylates with restricted homologue distribution and alkyl-oligoglucosides as well as electrolytes, such as sodium chloride or ammonium chloride.

Suitable cationic polymers are, for example, cationic cellulose derivatives, for example a quarternised hydroxymethyl cellulose obtainable under the name Polymer JR 400® from Amerchol, cationic starch, copolymers of diallylammonium salts and acrylamides, quaternised vinylpyrrolidone/vinyl imidazole polymers, for example Luviquat® (BASF), condensation products of polyglycols and amines, quaternised collagen polypeptides, for example lauryldimonium hydroxypropyl hydrolyzed collagen (Lamequat®L/Grünau), quaternised wheat polypeptides, polyethyleneimine, cationic silicone polymers, for example amidomethicones, copolymers of adipic acid and dimethylaminohydroxypropyldiethylenetriamine (Cartaretin®/Sandoz), copolymers of acrylic acid with dimethyldiallylammonium chloride (Merquat® 550/Chemviron), polyaminopolyamides, as described, for example, in FR-A-2 252 840, and the crosslinked water-soluble polymers thereof, cationic chitin derivatives, for example quaternised chitosan, optionally distributed as microcrystals; condensation products of dihaloalkyls, for example dibromobutane, with bisdialkylamines, for example bisdimethylamino-1,3-propane, cationic guar gum, for example Jaguar® C-17, Jaguar® C-16 from Celanese, quaternised ammonium salt polymers, for example Mirapol® A-15, Mirapol® AD-1, Mirapol® AZ-1 from Miranol.

Suitable anionic, zwitterionic, amphoteric and non-ionic polymers are for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyltrimethylammonium chloride/acrylate copolymers, octyl acrylamide/methyl methacrylate/tert-butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinyl caprolactam terpolymers and also optionally derivatised cellulose ethers and silicones.

Suitable silicone compounds are, for example, dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Also suitable are simethicones, which are mixtures of dimethicones having an average chain length of from 200 to 300 dimethylsiloxane units with hydrogenated silicates. A detailed survey by Todd et al. of suitable volatile silicones may in addition be found in Cosm. Toil. 91, 27 (1976).

Typical examples of fats are glycerides, and as waxes there come into consideration, inter alia, beeswax, carnauba wax, candelilla wax, montan wax, paraffin wax, hydrogenated castor oils and fatty acid esters or microwaxes solid at room temperature optionally in combination with hydrophilic waxes, e.g. cetyl stearyl alcohol or partial glycerides. Metal salts of fatty acids, for example magnesium, aluminum and/or zinc stearate or ricinoleate, may be used as stabilizers.

Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Suitable deodorizing active ingredients are for example, antiperspirants like aluminum chlorohydrates (see J. Soc. Cosm. Chem. 24, 281 (1973)). Aluminum chlorohydrate corresponding to formula $Al_2(OH)_5Cl \times 2.5\ H_2O$, known and commercially available under the trade mark Locron® of Hoechst AG, Frankfurt (FRG), is especially preferred (see J. Pharm. Pharmacol. 26, 531 (1975)). Beside the chlorohydrates, it is also possible to use aluminium hydroxy-acetates and acidic aluminium/zirconium salts. Esterase inhibitors may be added as further deodorising active ingredients. Such inhibitors are preferably trialkyl citrates, such as trimethyl citrate, tripropyl citrate, triisopropyl citrate, tributyl citrate and especially triethyl citrate (Hydagen® CAT, Henkel KGaA, Düsseldorf/FRG), which inhibit enzyme activity and hence reduce odor formation. Further suitable esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Antibacterial active ingredients that influence the microbial flora and kill, or inhibit the growth of, sweat-decomposing bacteria can likewise be present in the preparations (especially in stick preparations). Examples include chitosan, phenoxyethanol and chlorhexidine gluconate. 5-Chloro-2-(2,4-dichlorophenoxy)-phenol (Irgasan®, BASF has also proved especially effective.

Customary film formers include, for example, chitosan, microcrystalline chitosan, quaternised chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds. Suitable swelling agents for aqueous phases are montmorillonites, clay mineral substances, Pemulen and also alkyl-modified types of Carbopol (Goodrich). Further suitable polymers and swelling agents can be found in the review by R. Lochhead in Cosm. Toil. 108, 95 (1993).

For improvement of the flow behavior it is also possible to employ hydrotropic agents, for example ethanol, isopropyl alcohol or polyols. Suitable polyols for that purpose comprise preferably from 2 to 15 carbon atoms and at least two hydroxy groups.

The polyols may also contain further functional groups, especially amino groups, and/or may be modified with nitrogen. Typical examples are as follows:
glycerol;
alkylene glycols, for example ethylene glycol, diethylene glycol, propylene glycol, butylene glycol, hexylene glycol and also polyethylene glycols having an average molecular weight of from 100 to 1000 Dalton;

technical oligoglycerol mixtures having an intrinsic degree of condensation of from 1.5 to 10, for example technical diglycerol mixtures having a diglycerol content of from 40 to 50% by weight;

methylol compounds, such as, especially, trimethylolethane, trimethylolpropane, trimethylolbutane, pentaerythritol and dipentaerythritol;

lower alkyl-glucosides, especially those having from 1 to 8 carbon atoms in the alkyl radical, for example methyl and butyl glucoside;

sugar alcohols having from 5 to 12 carbon atoms, for example sorbitol or mannitol;

sugars having from 5 to 12 carbon atoms, for example glucose or saccharose;

amino sugars, for example glucamine;

dialcohol amines, such as diethanolamine or 2-amino-1,3-propanediol.

Suitable preservatives include, for example, phenoxyethanol, formaldehyde solution, Parabens, pentanediol or sorbic acid and the further substance classes listed in Schedule 6, Parts A and B of the Cosmetics Regulations.

Suitable perfume oils are mixtures of natural and/or synthetic aromatic substances. Representatives of natural aromatic substances are, for example, extracts from blossom (lilies, lavender, roses, jasmine, neroli, ylang-ylang), from stems and leaves (geranium, patchouli, petitgrain), from fruit (aniseed, coriander, carraway, juniper), from fruit peel (bergamot, lemons, oranges), from roots (mace, angelica, celery, cardamom, costus, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, olibanum, opoponax). Animal raw materials also come into consideration, for example civet and castoreum. Typical synthetic aromatic substances are, for example, products of the ester, ether, aldehyde, ketone, alcohol or hydrocarbon type.

Aromatic substance compounds of the ester type are, for example, benzyl acetate, phenoxyethyl isobutyrate, p-tert-butylcyclohexyl acetate, linalyl acetate, dimethyl-benzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, α-isomethylionone and methyl cedryl ketone; the alcohols include, for example, anethol, citronellol, eugenol, isoeugenol, geraniol, linalool, phenyl ethyl alcohol and terpinol; and the hydrocarbons include mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, galbanum oil, labolanum oil and lavandin oil. Preference is given to the use of bergamot oil, dihydromyrcenol, lilial, lyral, citronellol, phenyl ethyl alcohol, α-hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, β-damascone, bourbon geranium oil, cyclohexyl salicylate, vertofix coeur, iso-E-Super, Fixolide NP, evernyl, iraldein gamma, phenylacetic acid, geranyl acetate, benzyl acetate, rose oxide, romillat, irotyl and floramat alone or in admixture with one another.

Suitable colorants that are permitted for cosmetic purposes are for example published in "Kosmetische Färbemittel" of the Farbstoffkommission der Deutschen Forschungsgemeinschaft, Verlag Chemie, Weinheim, 1984, pages 81 to 106 may be used. The colorants are generally used in concentrations of from 0.001 to 0.1% by weight, based on the total mixture. Typical examples of bacteria-inhibiting agents are preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide).

A large number of aromatic substances and ethereal oils also have antimicrobial properties. Typical examples are the active ingredients eugenol, menthol and thymol in clove oil, mint oil and thyme oil. A natural deodorizing agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% by weight, based on the solids content of the cosmetic composition according to the present invention.

The cosmetic compositions according to the present invention may furthermore contain as adjuvants anti-foams, such as silicones, structurants, such as maleic acid, solubilizers, such as ethylene glycol, propylene glycol, glycerol or diethylene glycol, opacifiers, such as latex, styrene/PVP or styrene/acrylamide copolymers, complexing agents, such as EDTA, NTA, β-alaninediacetic acid or phosphonic acids, propellants, such as propane/butane mixtures, $N_2O$, dimethyl ether, $CO_2$, $N_2$ or air, so-called coupler and developer components as oxidation dye precursors, thioglycolic acid and derivatives thereof, thiolactic acid, cysteamine, thiomalic acid or α-mercaptoethanesulfonic acid as reducing agents or hydrogen peroxide, potassium bromate or sodium bromate as oxidizing agents.

Insect repellents are for example, N,N-diethyl-m-toluamide, 1,2-pentanediol or insect repellent 3535.

Suitable self-tanning agents are dihydroxyacetone, erythrulose or mixtures of dihydroxyacetone and erythrulose.

Cosmetic formulations according to the invention are contained in a wide variety of cosmetic preparations, especially the following preparations:

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eye shadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

light-protective preparations, such as sun milks, lotions, creams or oils, sunblocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

The final formulations may exist in a wide variety of presentation forms, for example:

in the form of liquid preparations as a W/O, O/W, O/W/O, W/O/W or PIT emulsion and all kinds of microemulsions, in the form of a gel, in the form of an oil, a cream, milk or lotion, in the form of a powder, a lacquer, a tablet or make-up, in the form of a stick, in the form of a spray (spray with propellant gas or pump-action spray) or an aerosol, in the form of a foam, or in the form of a paste.

Important cosmetic compositions for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection oils, sun protection milks and sun protection preparations in the form of a spray.

A. Examples for UV Filters and UV Filter Combinations According to the Present Invention Methods
Calculation of Spectral Transmittance $T(\lambda)$ of Sunscreens For calculation of the spectral transmittance $T(\lambda)$ of sunscreens with given filter compositions, a simulation tool is used. The tool is based on the following elements: a database with UV spectra of the relevant UV filters (given as decade molar extinction coefficients), a mathematical description of the irregularity profile of the sunscreen film on the skin, consideration of changes in UV filter concentration due to photo-instabilities, and consideration of formulation influences like the distribution of the UV filters in the oil and water phase of an emulsion.

Determination of SPF (Erythema Attenuation) and Attenuation Factor of Pre-Vitamin D Formation $AF_{vd}$ It's known from scientific literature that whole body exposure to 1 MED erythemal radiation exposure (Minimum Erythema Dose, this is the minimum amount of UV-B radiation after 24 h exposure)=250 J/m² erythemal radiant exposure is equivalent to an oral intake of about 10,000 IU vitamin $D_3$. For maximum solar input (according to COLIPA, sun in zenith, cloudless sky) it takes about 20 minutes to receive 1 MED. The recommended intake of vitamin $D_3$ ranges from 1,000 up to 4,000 IU/day. A daily supply of 2000 IU/day are recommended by the DGE (Deutsche Gesellschaft für Ernährung 2011). This recommendation relates to a lack of endogeneous/epidermal vitamin $D_3$ production, e.g. due to no exposure to UV radiation. This amount of Vitamin D3 can be produced in skin after f 20/5=4 minutes under the conditions that the unprotected skin is exposed to the above mentioned maximum solar input. Sunscreens attenuate the erythema irradiation and vitamin $D_3$-effective radiation.

MED=Minimum Erythema Dose=the minimum amount of UVB radiation [J/m²] that produces a first redness on skin 24 hours after exposure=250 J/m² erythemal radiation (standardized value) 1 IU=25 ng Vit $D_3$.

The SPF is calculated according to the following formula $$SPF = \frac{\int_{200}^{400} S(\lambda)s_{er}(\lambda)d\lambda}{\int_{200}^{400} S(\lambda)s_{er}(\lambda)T(\lambda)d\lambda}$$

By analogy to the SPF the attenuation factor for vitamin $D_3$-effective radiation $AF_{PVD}$ is defined as $$\boxed{AF_{PVD}} = \frac{\int E_\lambda(\lambda)SPVD(\lambda)d\lambda}{\int E_\lambda(\lambda)s_{PVD}(\lambda)T(\lambda)d\lambda}$$

$E(\lambda)$ spectral solar irradiance, $T(\lambda)$ spectral transmittance of a given sunscreen and both, the $s_{er}(\lambda)$ action spectrum of erythema $s_{pvd}(\lambda)$ action spectrum of vitamin $D_3$ formation in the skin.

Calculation of $E_{er}$, $E_{VD}$, $E_{VD}/E_{er}$, SPF, $AF_{VD}$ using the BASF Sunscreen Simulator: (www.basf.com/sunscreen-simulator; Herzog, B.; Osterwalder, U. In Silico Determination of Topical Sun Protection. Cosm Sci Tech. 2011; 62: 1-8.

The exposure time $t_{PVD}$ for producing the equivalent amount of the recommended vitamin $D_3$ intake of 2,000 IU with or without a sunscreen is $$t_{PVD} = 4 \times AF_{PVD} \text{ minutes}$$

when the protected skin is exposed to the above mentioned maximum solar input.

The attenuation factors $AF_{PVD}$ and the exposure times $t_{PVD}$ for the some examples of sunscreens are given in table 4.

Examples of filter compositions are chosen to achieve sun protection factors (abbreviated as SPF) of 6, 15, and 30.
Results

EXAMPLE A1: SPF 6 SUNSCREENS

Table 1 shows the compositions as well as the calculated values of SPF, $E_{pvd}/E_{er}$ ratio, UVA-PF, UVA-PF/SPF-ratio and critical wavelength CW for four SPF 6 sunscreens as explained above.

TABLE 1

UV filter compositions for SPF 6 with different levels of $E_{pvd}/E_{er}$ ratio and UVA protection

|  | Type | filter composition | SPF | $E_{pvd}/E_{er}$ | UVA-PF | UVA-PF/SPF | CW [nm] |
|---|---|---|---|---|---|---|---|
| F3 | A1.3 | 0.6% EHMC<br>1% MBBT<br>1% BEMT<br>1% DHHB | 7.2 | 1.94 | 7.1 | 0.99 | 377 |
| F4 | A1.4 | 7.5% DHHB,<br>3% BMDBM | 7.1 | 2.17 | 16.4 | 2.32 | 379 |

FIG. 3 shows the spectral transmittances of sunscreen films referring to the four different types of UV filter compositions leading to SPF 6.

EXAMPLE A2: SPF 15 SUNSCREENS

Table 2 shows the compositions as well as the calculated values of SPF, $E_{pvd}/E_{er}$ ratio, UVA-PF, UVA-PF/SPF-ratio and critical wavelength CW for four SPF 15 sunscreens.

TABLE 2

UV filter compositions for SPF 15 with different levels of $E_{pvd}/E_{er}$ ratio and UVA protection

| Type | filter composition | SPF | $E_{pvd}/E_{er}$ | UVA-PF | UVA-PF/SPF | CW [nm] |
|---|---|---|---|---|---|---|
| A2.3 | 2% MBBT, 2% BEMT, 2% BMDBM, 2.5% OCR | 15.7 | 1.91 | 15.6 | 0.99 | 378 |
| A2.4 | 3% BMDBM, 3.1% MBBT, 10% DHHB | 15.5 | 2.11 | 30.2 | 1.95 | 380 |

In FIG. 4 the simulated spectral transmittances of sunscreen films referring to the four different types of UV filter compositions leading to SPF 15 are depicted.

EXAMPLE A3: SPF 30 SUNSCREENS

Table 3 shows the compositions and the calculated values of SPF, $E_{pvd}/E_{er}$ ratio, UVA-PF, UVA-PF/SPF-ratio and critical wavelength CW for four SPF 30 sunscreens

TABLE 3

UV filter compositions for SPF 30 with different levels of $E_{pvd}/E_{er}$ ratio and UVA protection

| Type | filter composition | SPF | $E_{pvd}/E_{er}$ | UVA-PF | UVA-PF/SPF | CW [nm] |
|---|---|---|---|---|---|---|
| A3.3 | 2.2% PBSA, 3% BEMT, 4.5% MBBT, 4.5% DHHB | 33.2 | 1.84 | 33.5 | 1.01 | 378 |
| A3.4 | 1.9% BEMT, 3% BMDBM, 7.4% MBBT, 10% DHHB | 33.1 | 2.00 | 49.5 | 1.50 | 380 |

FIG. 4 shows the simulated spectral transmittances of sunscreen films referring to the four different types of UV filter compositions leading to SPF 30.

The examples A3.3 and A3.4 demonstrate that the transmittance of sunscreens for vitamin $D_3$-effective radiation can be optimized even if the SPF is the same.

EXAMPLE A4: DETERMINATION OF RECOMMENDED AMOUNT OF VITAMIN D/DAY

The exposure time $t_{PVD}$ for getting the recommended Vitamin D intake of 2000 IU/day is $t_{PVD}=4 \times AF_{PVD}$ minutes when the protected skin is exposed to the above mentioned maximum solar input. The attenuation factors $AF_{PVD}$ and the exposure times $t_{PVD}$ for the 4 examples of sunscreens are given in table 4.

TABLE 4

Attenuation factors $AF_{PVD}$ for vitamin $D_3$-effective radiation and exposure times $t_{PVD}$ needed per day for getting the recommended amount of 2000 IU vitamin $D_3$/day regarding 4 variations of sunscreens with SPF 6, 15 and 30 respectively

| Sunscreen type | SPF | 6 | 15 | 30 |
|---|---|---|---|---|
| 1 (state of the art) | $AF_{PVD}$ | 10.7 | 40.2 | 67.0 |
| | $t_{PVD}$ [min] | 42.8 | 160.8 | 268 |
| 2 (state of the art) | $AF_{PVD}$ | 7.8 | 16.2 | 34.0 |
| | $t_{PVD}$ [min] | 31.2 | 64.8 | 136 |
| 3 | $AF_{PVD}$ | 7.2 | 15.4 | 33.1 |
| | $t_{PVD}$ [min] | 28.8 | 61.6 | 132.4 |
| 4 | $AF_{PVD}$ | 6.1 | 13.7 | 30.6 |
| | $t_{PVD}$ [min] | 23.1 | 52.2 | 116.6 |

The exposure times $t_{PVD}$ for sun exposure with sunscreens e.g. with SPF=30 are with about 2 hours within the usual time frame of sun bathers. Thus it makes really sense to optimize sunscreens in terms of low attenuation factors $AF_{PVD}$.

| Type | Weight [%] | UV Filter Composition | SPF | $E_{vitD}/E_{er}$ |
|---|---|---|---|---|
| A2.4 | 4 | Methylene Bis-Benzotriazolyl Tetramethyl Butylphenol | 15.7 | 2.00 |
| | 2 | Bis-Ethylhexyloxyphenol Methoxyphenyl Triazine | | |
| | 8 | 1,4-(2-(4-diethylamino-2-hydroxybenzoyl)benzoyl)-piperazine | | |
| | 5 | Aqueous dispersion of Bis-Ethylhexyloxyphenol Methoxyphenyl Triazine/Polymethyl Methacrylate | | |
| A3.3 | 20 | 1,4-(2-(4-diethylamino-2-hydroxybenzoyl)benzoyl)-piperazine | 32.9 | 1.96 |
| | 2 | Bis-Ethylhexyloxyphenol Methoxyphenyl Triazine | | |
| | 3 | Diethylamino Hydroxybenzoyl Hexyl Benzoate | | |
| | 2 | Ethylhexyl Triazone | | |
| | 7.5 | Aqueous dispersion of Bis-Ethylhexyloxyphenol Methoxyphenyl Triazine/Polymethyl Methacrylate | | |
| A5.3 | 1 | Phenyl Benzimidazole Sulfonic Acid | 61.2 | 1.94 |
| | 3 | Ethylhexyl Triazone | | |
| | 2 | Bis-Ethylhexyloxyphenol Methoxyphenyl Triazine | | |
| | 6 | Methylene Bis-Benzotriazolyl Tetramethyl Butylphenol | | |
| | 8 | Diethylamino Hydroxybenzoyl Hexyl Benzoate | | |
| | 20 | 1,4-(2-(4-diethylamino-2-hydroxybenzoyl)benzoyl)piperazine | | |
| | 10 | Aqueous dispersion of Bis-Ethylhexyloxyphenol Methoxyphenyl Triazine/Polymethyl Methacrylate | | |
| A3.3 | 12 | Methylene Bis-Benzotriazolyl Tetramethyl Butylphenol | 30.1 | 1.82 |
| | 12 | Tris-Biphenyl Triazine | | |

-continued

| Type | Weight [%] | UV Filter Composition | SPF | $E_{vitD}/E_{er}$ |
|---|---|---|---|---|
| A2.4 | 14 | Methylene Bis-Benzotriazolyl Tetramethyl Butylphenol | 15.0 | 2.04 |
|  | 20 | 1,4-(2-(4-diethylamino-2-hydroxybenzoyl)benzoyl)piperazine |  |  |
| A3.3 | 12 | Methylene Bis-Benzotriazolyl Tetramethyl Butylphenol | 30.0 | 1.83 |
|  | 5 | Titanium Dioxide |  |  |
| A3.4 | 16 | Methylene Bis-Benzotriazolyl Tetramethyl Butylphenol | 30.7 | 2.03 |
|  | 3 | Titanium Dioxide |  |  |
|  | 4 | Diethylamino Hydroxybenzoyl Hexyl Benzoate |  |  |
|  | 20 | 1,4-(2-(4-diethylamino-2-hydroxybenzoyl)benzoyl)piperazine |  |  |
| A3.3 | 14 | Methylene Bis-Benzotriazolyl Tetramethyl Butylphenol | 30.9 | 1.84 |
|  | 5 | Drometrizole trisiloxane |  |  |
| A2.3 | 2 | Bis-Ethylhexyloxyphenol Methoxyphenyl Triazine | 15.6 | 1.86 |
|  | 5 | Compound of formula (PBT2) |  |  |
|  | 2 | 1,4-(2-(4-diethylamino-2-hydroxybenzoyl)benzoyl)-piperazine |  |  |
| A2.4 | 2 | Bis-Ethylhexyloxyphenol Methoxyphenyl Triazine | 16.3 | 2.02 |
|  | 3 | Compound of formula (PBT2) |  |  |
|  | 16 | 1,4-(2-(4-diethylamino-2-hydroxybenzoyl)benzoyl)-piperazine |  |  |
| A4.3 | 16 | Methylene Bis-Benzotriazolyl Tetramethyl Butylphenol | 50.5 | 1.81 |
|  | 3.5 | Titanium Dioxide |  |  |
|  | 6% | Compound of formula (PBT2) |  |  |
|  | 6 | Drometrizole trisiloxane |  |  |
| A2.4 | 14 | Methylene Bis-Benzotriazolyl Tetramethyl Butylphenol | 30.7 | 1.85 |
|  | 3 | Titanium Dioxide |  |  |
|  | 4 | Compound of formula (PBT2) |  |  |
| A5.3 | 16 | Methylene Bis-Benzotriazolyl Tetramethyl Butylphenol | 60.2 | 1.89 |
|  | 3.5 | Titanium Dioxide |  |  |
|  | 6 | BTEM |  |  |
|  | 6 | Drometrizole trisiloxane |  |  |
|  | 10 | 1,4-(2-(4-diethylamino-2-hydroxybenzoyl)benzoyl)piperazine |  |  |
| A1.4 | 9 | Diethylamino Hydroxybenzoyl Hexyl Benzoate | 6.3 | 2.18 |
| A1.3 | 3 | Bis-Ethylhexyloxyphenol Methoxyphenyl Triazine | 7.3 | 1.87 |
| A2.4 | 3 | Bis-Ethylhexyloxyphenol Methoxyphenyl Triazine | 15.6 | 2.05 |
|  | 20 | 1,4-(2-(4-diethylamino-2-hydroxybenzoyl)benzoyl)-piperazine |  |  |
| A3.3 | 2 | Octocrylene | 30.6 | 1.94 |
|  | 2 | Butyl Methoxy Dibenzoyl Methane |  |  |
|  | 2.5 | Bis-Ethylhexyloxyphenol Methoxyphenyl Triazine |  |  |
|  | 8 | Terephthalylidene Dicamphor Sulfonic Acid |  |  |
|  | 12 | 1,4-(2-(4-diethylamino-2-hydroxybenzoyl)benzoyl)-piperazine |  |  |
| A2.3 | 3 | Polisilicone-15 | 16.3 | 1.87 |
|  | 2 | Bis-Ethylhexyloxyphenol Methoxyphenyl Triazine |  |  |
|  | 4 | Disodium Phenyl Dibenzimidazole Tetrasulfonate |  |  |
| A2.3 | 1 | Diethylhexyl Butamido Triazone | 15.5 | 1.81 |
|  | 2 | Bis-Ethylhexyloxyphenol Methoxyphenyl Triazine |  |  |
|  | 3 | Disodium Phenyl Dibenzimidazole Tetrasulfonate |  |  |
| A2.3 | 25 | Zinc Oxide | 15.7 | 1.92 |
|  | 1.2 | Titanium Dioxide |  |  |
| A3.4 | 9 | Methylene Bis-Benzotriazolyl Tetramethyl Butylphenol | 31.2 | 2.01 |
|  | 1.5 | Bis-Ethylhexyloxyphenol Methoxyphenyl Triazine |  |  |
|  | 25 | Zinc Oxide |  |  |
|  | 20 | 1,4-(2-(4-diethylamino-2-hydroxybenzoyl)benzoyl)-piperazine |  |  |
| A1.3 | 15 | Zinc Oxide | 6.6 | 1.97 |
| A3.3 | 4 | Ethylhexyl Salicylate | 30.9 | 1.89 |
|  | 2 | Butyl Methoxy Dibenzoyl Methane |  |  |
|  | 1.5 | Bis-Ethylhexyloxyphenol Methoxyphenyl Triazine |  |  |
|  | 1.5 | Methylene Bis-Benzotriazolyl Tetramethyl Butylphenol |  |  |
|  | 3 | Benzophenone-3 |  |  |
|  | 3 | Titanium Dioxide |  |  |
|  | 16 | 1,4-(2-(4-diethylamino-2-hydroxybenzoyl)benzoyl)-piperazine |  |  |
| A3.3 | 4 | Ethylhexyl Salicyate | 31.4 | 1.89 |
|  | 2 | Butyl Methoxy Dibenzoyl Methane |  |  |
|  | 1.5 | Tinosorb ®S |  |  |
|  | 1.5 | Methylene Bis-Benzotriazolyl Tetramethyl Butylphenol |  |  |
|  | 3 | Benzophenone-4 |  |  |
|  | 3 | Titanium Dioxide |  |  |
|  | 16 | 1,4-(2-(4-diethylamino-2-hydroxybenzoyl)benzoyl)-piperazine |  |  |

-continued

| Type | Weight [%] | UV Filter Composition | SPF | $E_{vitD}/E_{er}$ |
|---|---|---|---|---|
| A3.3 | 4 | Homomenthyl Salicyate | 30.8 | 1.90 |
|  | 2 | Butyl Methoxy Dibenzoyl Methane |  |  |
|  | 1.5 | Bis-Ethylhexyloxyphenol Methoxyphenyl Triazine |  |  |
|  | 1.5 | Methylene Bis-Benzotriazolyl Tetramethyl Butylphenol |  |  |
|  | 3 | Benzophenone-4 |  |  |
|  | 3 | Titanium Dioxide |  |  |
|  | 16 | 1,4-(2-(4-diethylamino-2-hydroxybenzoyl)benzoyl)-piperazine |  |  |
| A1.4 | 5 | Terephthalylidene Dicamphor Sulfonic Acid | 6.06 | 2.03 |
| A2.3 | 2 | Octocrylene | 15.2 | 1.91 |
|  | 1 | Butyl Methoxy Dibenzoyl Methane |  |  |
|  | 4 | Terephthalylidene Dicamphor Sulfonic Acid |  |  |
|  | 1 | Benzophenone-3 |  |  |
|  | 5 | Menthyl Anthranilate |  |  |
| A3.3 | 3 | Bis-Ethylhexyloxyphenol Methoxyphenyl Triazine | 30.0 | 1.96 |
|  | 5 | Diethylamino Hydroxybenzoyl Hexyl Benzoate |  |  |
|  | 5 | Compound of formula (BM9) |  |  |
|  | 12 | 1,4-(2-(4-diethylamino-2-hydroxybenzoyl)benzoyl)piperazine |  |  |
| A3.4 | 3 | Bis-Ethylhexyloxyphenol Methoxyphenyl Triazine | 30.1 | 2.01 |
|  | 6 | Diethylamino Hydroxybenzoyl Hexyl Benzoate |  |  |
|  | 4 | Compound of formula (BM9) |  |  |
|  | 16 | 1,4-(2-(4-diethylamino-2-hydroxybenzoyl)benzoyl)piperazine |  |  |
| A3.3 | 3 | Bis-Ethylhexyloxyphenol Methoxyphenyl Triazine | 30.1 | 1.87 |
|  | 10 | Diethylamino Hydroxybenzoyl Hexyl Benzoate |  |  |
|  | 3 | Ethylhexyl Triazone |  |  |
| A0.3 | 0.5 | Bis-Ethylhexyloxyphenol Methoxyphenyl Triazine | 2.1 | 1.95 |

B. Examples for Cosmetic Formulations

Example B1: Type 1.3, SPF = 6

|  | Trade Name | INCI Name | % w/w, as supplied |
|---|---|---|---|
| Part A | Uvinul ® A Plus | Diethylamino Hydroxybenzoyl Hexyl Benzoate (DHHB) | 1.00 |
|  | Uvinul ® MC 80 | Ethylhexyl Methoxycinnamate | 0.60 |
|  | Tinosorb ® S | Bis-Ethylhexyloxyphenol Methoxyphenyl Triazine | 1.00 |
|  | Cetiol ® AB | C12-15 Alkyl Benzoate | 8.00 |
| Part B | Water | Aqua | Qs to 100 |
|  | Butylene glycol | Butylene glycol | 2.50 |
|  | Mais PO4 PH "B" | Distarch phosphate | 2.00 |
|  | Tinovis ® GTC | Acrylates/beheneth-25 methylacrylate copolymer | 1.50 |
| Part C | Sodium hydroxide (30% solution) | Water (and) sodium hydroxide | Qs to pH 7 |
| Part D | Tinosorb ® M | Methylene Bis-Benzotriazolyl Tetramethyl-butylphenol | 1.00 |
|  | Ethanol 96% | Alcohol | 5.00 |

The formulation is prepared as follows: Parts A and B are prepared and separately heated to 80° C. Then part A is added to part B under stirring. After short homogenization part C is added under stirring. After cooling down to room temperature the ingredients of part D are added in the listed order.

Example B2: Type 1.4, SPF = 6

|  | Trade Name | INCI Name | % w/w as supplied |
|---|---|---|---|
| Part A | Cetiol ® CC | Dicaprylyl carbonate | 5.00 |
|  | Cetiol ® B | Dibutyl adipate | 4.00 |
|  | Cetiol ® C5 | Coco-caprylate | 3.00 |
|  | Cetiol ® AB | C12-15 Alkyl Benzoate | 5.00 |
|  | Sensiva SC 50 | Ethylhexyl glycerol | 0.50 |
|  | Parsol ® 1789 | Butyl Methoxydibenzoyl-methane | 3.00 |
|  | Uvinul ® A Plus | Diethylamino Hydroxybenzoyl Hexyl Benzoate | 7.5 |
| Part B | Water | Aqua | Qs to 100 |
|  | Glycerin 85% | Glycerol | 3.00 |
|  | Protectol PE | Phenoxyethanol | 1.00 |
|  | Eumulgin ® SG | Sodium Stearoyl Glutamate | 0.80 |
|  | Edeta ® BD | Disodium EDTA | 0.20 |
|  | Keltrol CG RD | Xanthan Gum | 0.20 |
| Part C | Tinovis ® ADE | sodium acrylates copolymer (and) hydrogenated poly-decene (and) PPG-1 tri-deceth-6 | 1.00 |

Example B2: Type 1.4, SPF = 6

|  | Trade Name | INCI Name | % w/w as supplied |
|---|---|---|---|
| Part D | Orgasol Caresse | Polyamide-5 | 3.00 |
|  | Sodium Hydroxide (30% solution) | Water (and) Sodium Hydroxide | 0.20 |

The formulation is prepared as follows: Part A is heated to 80° C., cooled down to room temperature and incorporated into part B under stirring. After homogenization (with an ultra-turrax type device) part C is added, again followed by homogenization. Finally the ingredients of part D are added and the formulation is homogenized again.

Example B3: Type 2.3, SPF = 15

|  | Trade Name | INCI Name | % w/w, as supplied |
|---|---|---|---|
| Part A | Parsoll ® 1789 | Butyl Methoxy Dibenzoyl Methane | 3.00 |
|  | Uvinul ® A plus | Diethylamino Hydroxybenzoyl Hexyl Benzoate | 10.00 |
|  | Cetiol ® AB | C12-15 Alkyl Benzoate | 8.00 |
| Part B | Water | Aqua | Qs to 100 |
|  | Butylene glycol | Butylene glycol | 2.50 |
|  | Mais PO4 PH "B" | Distarch phosphate | 2.00 |
|  | Tinovis ® GTC | Acrylates/beheneth-25 methylacrylate copolymer | 1.50 |
| Part C | Sodium hydroxide (30% solution) | Water (and) sodium hydroxide | Qs to pH 7 |
| Part D | Tinosorb ® M | Methylene Bis-Benzotriazolyl Tetramethyl-butylphenol | 3.10 |
|  | Ethanol 96% | Alcohol | 5.00 |

The formulation is prepared as follows: Parts A and B are prepared and separately heated to 80° C. Then part A is added to part B under stirring. After short homogenization part C is added under stirring. After cooling down to room temperature the ingredients of part D are added in the listed order.

Example B4: Type 2.4, SPF = 15

|  | Trade Name | INCI Name | % w/w, as supplied |
|---|---|---|---|
| Part A | Parsol ® 1789 | Butyl Methoxydibenzoyl-methane | 3.00 |
|  | Uvinul ® N 539 | Octocrylene | 2.50 |
|  | Tinosorb ® S | Bis-Ethylhexyloxyphenol Methoxyphenyl Triazine (BEMT) | 2.00 |
|  | Cetiol ® AB | C12-15 Alkyl Benzoate | 15.0 |
| Part B | Water | Aqua | Qs to 100 |
|  | Butylene glycol | Butylene glycol | 2.50 |
|  | Mais PO4 PH "B" | Distarch phosphate | 2.00 |
|  | Tinovis ® GTC | Acrylates/beheneth-25 methylacrylate copolymer | 1.50 |
| Part C | Sodium hydroxide (30% solution) | Water (and) sodium hydroxide | Qs to pH 7 |
| Part D | Tinosorb ® M | Methylene Bis-Benzotriazolyl Tetramethyl-butylphenol | 2.00 |
|  | Ethanol 96% | Alcohol | 3.00 |

The formulation is prepared as follows: Parts A and B are prepared and separately heated to 80° C. Then part A is added to part B under stirring. After short homogenization part C is added under stirring. After cooling down to room temperature the ingredients of part D are added in the listed order.

Example B5: Type 3.3, SPF = 30

|  | Trade Name | INCI Name | % w/w, as supplied |
|---|---|---|---|
| Part A | Uvinul ® A plus | Diethylamino Hydroxybenzoyl Hexyl Benzoate | 4.50 |
|  | Tinosorb ® S | Bis-Ethylhexyloxyphenol Methoxyphenyl Triazine | 3.00 |
|  | Cetiol ® AB | C12-15 Alkyl Benzoate | 12.0 |
|  | Cetiol ® B | Dibutyl adipate | 5.00 |
| Part B | Water | Aqua | Qs to 100 |
|  | Butylene glycol | Butylene glycol | 2.50 |
|  | Mais PO4 PH "B" | Distarch phosphate | 2.00 |
|  | Tinovis ® GTC | Acrylates/beheneth-25 methylacrylate copolymer | 1.50 |
| Part C | Water | Aqua | 9.00 |
|  | Eusolex ® 232 | Phenyl Benzimidazole Sulfonic Acid | 3.00 |
|  | Tris Amino Ultra Pur | Tromethamine | Qs to pH 7 |
| Part D | Tinosorb ® M | Methylene Bis-Benzotriazolyl Tetramethyl-butylphenol | 4.50 |
|  | Ethanol 96% | Alcohol | 3.00 |

The formulation is prepared as follows: Parts A and B are prepared and separately heated to 80° C. Then part A is added to part B under stirring. After short homogenization part C is added under stirring. After cooling down to room temperature the ingredients of part D are added in the listed order.

Example B6: Type 3.4, SPF = 30

|  | Trade Name | INCI Name | % w/w, as supplied |
|---|---|---|---|
| Part A | Parsol ® 1789 | Butyl Methoxydibenzoyl-methane | 3.00 |
|  | Uvinul ® A plus | Diethylamino Hydroxybenzoyl Hexyl Benzoate | 10.0 |
|  | Tinosorb ® S | Bis-Ethylhexyloxyphenol Methoxyphenyl Triazine | 1.90 |
|  | Cetiol ® AB | C12-15 Alkyl Benzoate | 14.0 |
|  | Cetiol ® B | Dibutyl adipate | 8.00 |
| Part B | Water | Aqua | Qs to 100 |
|  | Butylene glycol | Butylene glycol | 2.50 |
|  | Mais PO4 PH "B" | Distarch phosphate | 2.00 |
|  | Tinovis ® GTC | Acrylates/beheneth-25 methylacrylate copolymer | 1.50 |
| Part C | Sodium hydroxide (30% solution) | Water (and) sodium hydroxide | Qs to pH 7 |

Example B7: Type 3.4, SPF = 30

|  | Trade Name | INCI Name | % w/w, as supplied |
|---|---|---|---|
| Part D | Tinosorb ® M | Methylene Bis-Benzotriazolyl Tetramethylbutylphenol | 7.40 |
|  | Ethanol 96% | Alcohol | 3.00 |

The formulation is prepared as follows: Parts A and B are prepared and separately heated to 80° C. Then part A is added to part B under stirring. After short homogenization part C is added under stirring. After cooling down to room temperature the ingredients of part D are added in the listed order.

The invention claimed is:
1. A sunscreen formulation comprising at least one UV filter (A) selected from the group consisting of:
    (a) 0.1-40% by weight of triazine derivatives;
    (b) 0.1-30% by weight of cinnamic acid derivatives;
    (c) 0.1-10% by weight of bis-resorcinyl triazines;
    ($f_1$) 0.1-10% by weight of phenyl benzimidazole sulfonic acid;
    ($i_5$) 0.1-10% by weight of 4-Methylbenzylidene Camphor;
    (h) 0.1-10% by weight of benzoyl piperazine derivatives;
    (j) 0.1-10% by weight of benzoxazole derivatives;
    (k) 0.1-20% by weight of diarylbutadiene derivatives;
    (l) 0.1-30% by weight of phenyl benzotriazole derivatives;
    (n) 0.1-20% by weight of benzylidene malonates;
    ($o_3$) 0.1-15% by weight of TEA-Salicylate;
    (r) 0.1-10% by weight of imidazoline derivatives;
    (u) 0.1-50% by weight of inorganic UV filters selected from metal oxides;
    (v) 0.1-20% by weight of naphthalates; and
    (w) 0.1-20% by weight of merocyanine derivatives;
    and optionally comprising at least one UV filter (B) selected from the group consisting of:
    (d) 0.1-20% by weight of aminobenzophenone derivatives;
    (e) 0.1-5% by weight of dibenzoylmethane derivatives;
    (g) 0.1-1% by weight of β,β-Diphenylacrylate derivatives;
    (i) 0.1-10% by weight of camphor derivatives different from ($i_5$);
    (o) 0.1-35% by weight of salicylate derivatives different from ($o_3$);
    (p) 0.1-10% by weight of anthranilate derivatives; and
    (s) 0.1-10% by weight of benzalmalonate derivatives;
    wherein the type and amount of the at least one UV filter (A) and optionally at least one UV filter (B) are selected to arrive at a ratio R of the effective irradiance for previtamin $D_3$ formation $E_{pvd}$ to the effective irradiance for erythema formation $E_{er}$ on the skin is at least 1.8, and
    for increasing the transmittance of UV radiation on human skin for the production of cholecalciferol (previtamin $D_3$) and simultaneously for the use in a method for protecting the human skin against UV radiation when exposed to the sun, which method comprises applying said sunscreen formulation to the skin.
2. The sunscreen formulation of claim 1, wherein the sunscreen formulation has an SPF of at least 2.
3. The sunscreen formulation of claim 1, wherein the sunscreen formulation has an SPF of at least 6.
4. The sunscreen formulation of claim 1, wherein the at least one UV filter (A) is selected from the group consisting of:
    ($a_1$) ethylhexyl triazone;
    ($a_2$) tris-bephenyl triazine;
    ($a_3$) diethylhexyl butamido triazone;
    ($c_1$) bis-ethylhexyloxyphenol methoxyphenyl triazine;
    ($c_2$) aqueous dispersion of bis-ethylhexyloxyphenol methoxyphenyl triazine/polymethyl methacrylate;
    ($f_1$) phenyl benzimidazole sulfonic acid;
    ($h_1$) 1,4-(2-(4-diethylamino-2-hydroxybenzoyl)benzoyl) piperazine;
    ($l_1$) methylene bis-benzotriazolyl tetramethyl butylphenol;
    ($l_2$) drometrizole trisiloxane;
    ($l_6$) 2-(2h-benzotriazol-2-yl)-6-(2-ethylhexyloxymethyl)-4-methyl-phenol;
    ($n_1$) compound of formula (BM9);
    ($u_1$) zinc oxide;
    ($u_3$) titanium dioxide; and
    mixtures thereof;
    and wherein the optional at least one UV filter (B) is selected from the group consisting of:
    ($d_1$) diethylamino hydroxybenzoyl hexyl benzoate;
    ($e_1$) butyl methoxy dibenzoyl methane;
    ($g_1$) octocrylene;
    ($i_1$) terephthalylidene dicamphor sulfonic acid;
    ($o_1$) ethylhexyl salicylate;
    ($o_4$) homosalate;
    ($p_1$) menthyl anthranilate;
    ($s_1$) polysilicone-15; and
    mixtures thereof.
5. The sunscreen formulation of claim 1,
    wherein the at least one UV filter (A) is selected from the group consisting of:
    ($b_1$) ethylhexyl methoxy cinnamate;
    ($c_1$) bis-ethylhexyloxyphenol methoxyphenyl triazine;
    ($l_1$) methylene bis-benzotriazolyl tetramethyl butylphenol;
    ($f_1$) phenyl benzimidazole sulfonic acid; and
    mixtures thereof;
    and wherein the optional at least one UV filter (B) is selected from the group consisting of
    ($d_1$) diethylamino hydroxybenzoyl hexyl benzoate;
    ($e_1$) butyl methoxy dibenzoyl methane;
    ($g_1$) octocrylene; and
    mixtures thereof.
6. The sunscreen formulation of claim 5, wherein the sunscreen formulation has an SPF of at least 6.
7. The sunscreen formulation of claim 1, wherein the at least one UV filter is selected from the group consisting of:
    ($c_1$) bis-ethylhexyloxyphenol methoxyphenyl triazine;
    ($l_1$) methylene bis-benzotriazolyl tetramethyl butylphenol; and
    mixtures thereof;
    and wherein the optional at least one UV filter (B) is selected from the group consisting of:
    ($d_1$) diethylamino hydroxybenzoyl hexyl benzoate;
    ($e_1$) butyl methoxy dibenzoyl methane; and
    mixtures thereof.
8. The sunscreen formulation of claim 1, wherein the at least one UV filter (A) is selected from the group consisting of:
    ($a_1$) 1-3% by weight of ethylhexyl triazone;
    ($b_1$) 1-3.5% by weight of ethylhexyl methoxycinnamate;
    ($c_1$) 0.6-10% by weight of bis-ethylhexyloxyphenol methoxyphenyl triazine;
    ($f_1$) 2-3% by weight of phenyl benzimidazole sulfonic acid;
    ($l_1$) 2-7.5% by weight of methylene bis-benzotriazolyl tetramethylbutylphenol;
    ($u_3$) 3.0-3.5% by weight of titanium dioxide;
    and mixtures thereof;
    and wherein the optional at least one UV filter (B) is selected from the group consisting of:
    ($d_1$) 0.8-10% by weight of diethylamino hydroxybenzoyl hexyl benzoate;
    ($e_1$) 2-3% by weight of butyl methoxydibenzoylmethane;
    ($g_1$) 2.0-2.5% by weight of octocrylene;
    and mixtures thereof.

9. The sunscreen formulation of claim 1, wherein the sunscreen comprises the UV filter combination of the UV filter (A):
- ($l_1$) methylene bis-benzotriazolyl tetramethyl butylphenol; and and optionally at least one UV filter (B) selected from the group consisting of:
- ($d_1$) diethylamino hydroxybenzoyl hexyl benzoate; and
- ($e_1$) butyl methoxy dibenzoyl methane;

wherein the sunscreen has a SPF of >15.

10. The sunscreen formulation of claim 1, wherein the sunscreen comprises the UV filter combination of the UV filters (A):
- ($c_1$) bis-ethylhexyloxyphenol methoxyphenyl triazine; and
- ($l_1$) methylene bis-benzotriazolyl tetramethyl butylphenol;

and optionally at least one UV filter (B) selected from the group consisting of:
- ($d_1$) diethylamino hydroxybenzoyl hexyl benzoate; and
- ($e_1$) butyl methoxy dibenzoyl methane; and
- mixtures thereof;

wherein the sunscreen has a SPF>30.

11. The sunscreen formulation of claim 1, wherein the UV filters are broadband (spectrum of 340 to 400 nm) UV filters comprising a UV filter (A) selected from the group consisting of:
- ($c_1$) bis-ethylhexyloxyphenol methoxyphenyl triazine;
- ($c_2$) aqueous dispersion of bis-ethylhexyloxyphenol methoxyphenyl triazine/polymethyl methacrylate;
- ($l_1$) methylene bis-benzotriazolyl tetramethyl butylphenol;
- ($l_2$) drometrizole trisiloxane;
- ($u_1$) zinc oxide; and
- mixtures thereof;

and optionally at least one UV filter (B) selected from the group consisting of:
- ($e_1$) butyl methoxy dibenzoyl methane;
- ($d_1$) diethylamino hydroxybenzoyl hexyl benzoate;
- ($i_1$) terephthalylidene dicamphor sulfonic acid;
- ($p_1$) menthyl anthranilate; and
- mixtures thereof.

12. The sunscreen formulation of claim 1, comprising a UV filter (A) selected from the group consisting of:
- (a) triazine derivatives;
- (b) cinnamic acid derivatives;
- (c) bis-resorcinyl triazines;
- ($f_1$) phenyl benzimidazole sulfonic acid;
- (h) benzoyl-piperazine derivatives;
- ($i_5$) 4-Methylbenzylidene Camphor;
- (l) phenyl benzotriazole derivatives;
- (n) benzylidene malonates;
- ($o_3$) TEA-Salicylate;
- (r) imidazoline derivatives;
- (u) inorganic UV filters selected from metal oxides;
- (v) naphthalates; and
- (w) merocyanine derivatives;

and wherein the optional at least one UV filter (B) is selected from the group consisting of:
- ($i_1$) terephthalylidene dicamphor sulfonic acid;

wherein the sunscreen formulation contains only one of the selected UV (A) filters.

13. The sunscreen formulation of claim 12, wherein the UV filters are broadband (spectrum of 340 to 400 nm) UV filters comprising a UV filter (A) selected from the group consisting of:
- ($c_1$) bis-ethylhexyloxyphenol methoxyphenyl triazine;
- ($c_2$) aqueous dispersion of bis-ethylhexyloxyphenol methoxyphenyl triazine/polymethyl methacrylate;
- ($l_1$) methylene bis-benzotriazolyl tetramethyl butylphenol; and
- ($u_1$) zinc oxide;

and wherein the optional at least one UV filter (B) is selected from the group consisting of:
- ($i_1$) terephthalylidene dicamphor sulfonic acid;

wherein the sunscreen formulation contains only one of the selected UV (A) filters.

14. The sunscreen formulation of claim 1, wherein the UV filters are particulate UV filters (A) selected from the group consisting of:
- ($a_2$) tris-biphenyl triazine;
- ($c_2$) aqueous dispersion of bis-ethylhexyloxyphenol methoxyphenyl triazine/polymethyl methacrylate;
- ($h_1$) 1,4-(2-(4-diethylamino-2-hydroxybenzoyl)benzoyl) piperazine;
- ($l_1$) methylene bis-benzotriazolyl tetramethyl butylphenol;
- ($u_1$) zinc oxide;
- ($u_3$) titanium dioxide; and
- mixtures thereof.

15. The sunscreen formulation of claim 1, wherein the UV filters are non-particulate UV filters (A) selected from the group consisting of:
- ($a_1$) ethylhexyl triazone;
- ($a_3$) diethylhexyl butamido triazone;
- ($c_1$) bis-ethylhexyloxyphenol methoxyphenyl triazine;
- ($f_1$) phenyl benzimidazole sulfonic acid;
- ($h_1$) 1,4-(2-(4-diethylamino-2-hydroxybenzoyl)benzoyl) piperazine;
- ($l_1$) methylene bis-benzotriazolyl tetramethyl butylphenol;
- (l2) drometrizole trisiloxane;
- (l6) 2-(2h-benzotriazol-2-yl)-6-(2-ethylhexyloxymethyl)-4-methyl-phenol;
- ($n_1$) compound of formula (BM9); and
- mixtures thereof;

and wherein the optional at least one UV filter (B) is selected from the group consisting of:
- ($d_1$) diethylamino hydroxybenzoyl hexyl benzoate;
- ($e_1$) butyl methoxy dibenzoyl methane;
- ($g_1$) octocrylene;
- ($i_1$) terephthalylidene dicamphor sulfonic acid;
- ($o_1$) ethylhexyl salicylate;
- ($o_4$) homosalate;
- ($p_1$) menthyl anthranilate; and
- ($s_1$) polysilicone-15; and
- mixtures thereof.

16. The sunscreen formulation of claim 1, wherein the type and amount of UV filters (A) and optionally (B) are selected to arrive at a ratio of the effective irradiance for vitamin D formation $E_{pvd}$ and the effective irradiance for erythema formation $E_{er}$ on the skin of >2.0.

17. The sunscreen formulation of claim 1, wherein the UV filters selected are ethylhexyl methoxycinnamate, methylene bis-benzotriazolyl tetramethylbutylphenol, bis-ethylhexyloxyphenol methoxyphenyl triazine, and optionally diethylamino hydroxybenzoyl hexyl benzoate.

18. A sunscreen formulation comprising a UV filter combination of:
- ($d_1$) diethylamino hydroxybenzoyl hexyl benzoate;
- ($l_1$) methylene bis-benzotriazolyl tetramethyl butylphenol; and
- ($e_1$) butyl methoxy dibenzoyl methane;

wherein the sunscreen formulation has an SPF of >15 and
wherein the amount of the UV filter combination is selected to arrive at a ratio R of the effective irradiance for previtamin $D_3$ formation $E_{pvd}$ to the effective irradiance for erythema formation $E_{er}$ on the skin is at least 1.8, for increasing the transmittance of UV radiation on human skin for the production of cholecalciferol (previtamin $D_3$) and simultaneously for the use in a method protecting the human skin against UV radiation when exposed to the sun, which method comprises applying said sunscreen formulation to the skin.

19. A sunscreen formulation comprising a UV filter combination of:
- ($c_1$) bis-ethylhexyloxyphenol methoxyphenyl triazine;
- ($d_1$) diethylamino hydroxybenzoyl hexyl benzoate;
- ($l_1$) methylene bis-benzotriazolyl tetramethyl butylphenol; and
- ($e_1$) butyl methoxy dibenzoyl methane;

wherein the sunscreen formulation has an SPF>30;
wherein the amount of the UV filter combination is selected to arrive at a ratio R of the effective irradiance for previtamin $D_3$ formation $E_{pvd}$ to the effective irradiance for erythema formation $E_{er}$ on the skin is at least 1.8, for increasing the transmittance of UV radiation on human skin for the production of cholecalciferol (previtamin $D_3$) and simultaneously for the use in a method protecting the human skin against UV radiation when exposed to the sun, which method comprises applying said sunscreen formulation to the skin.

* * * * *